(12) United States Patent
Abouelsoud et al.

(10) Patent No.: US 11,896,833 B2
(45) Date of Patent: Feb. 13, 2024

(54) GENERATING VOLTAGE-GRADIENT GEOMETRIES IN BIOLOGICAL TISSUE

(71) Applicants: Mohammed Abouelsoud, Mayfield Heights, OH (US); David J. Mishelevich, Playa Del Rey, CA (US)

(72) Inventors: Mohammed Abouelsoud, Mayfield Heights, OH (US); David J. Mishelevich, Playa Del Rey, CA (US)

(73) Assignee: U LLC, Mayfield Heights, OH (US)

( * ) Notice: Subject to any disclaimer, the term of this patent is extended or adjusted under 35 U.S.C. 154(b) by 0 days.

(21) Appl. No.: 18/064,270

(22) Filed: Dec. 11, 2022

(65) Prior Publication Data
US 2023/0241403 A1    Aug. 3, 2023

Related U.S. Application Data

(60) Provisional application No. 63/288,648, filed on Dec. 13, 2021.

(51) Int. Cl.
  *A61N 1/04*   (2006.01)
  *A61N 1/372*  (2006.01)
  *A61N 1/36*   (2006.01)

(52) U.S. Cl.
  CPC ......... *A61N 1/3727* (2013.01); *A61N 1/3606* (2013.01); *A61N 1/36139* (2013.01)

(58) Field of Classification Search
  CPC ................ A61N 1/3727; A61N 1/3606; A61N 1/36139; A61N 1/0534
  See application file for complete search history.

(56) References Cited

U.S. PATENT DOCUMENTS

| | | | |
|---|---|---|---|
| 2011/0130615 A1* | 6/2011 | Mishelevich | A61N 1/36078 607/45 |
| 2012/0245653 A1* | 9/2012 | Bikson | G16H 50/50 607/45 |
| 2017/0164862 A1* | 6/2017 | Dolev | A61B 5/291 |
| 2021/0370063 A1* | 12/2021 | Abouelsoud | A61N 1/36025 |

OTHER PUBLICATIONS

Seo, Moonsang, Eunjeong Lee, and Bruno B. Averbeck. "Action selection and action value in frontal-striatal circuits." Neuron 74.5 (2012): 947-960. [Elsevier, Netherlands] Section "Discussion" Paragraphs 3/5.

(Continued)

*Primary Examiner* — Eugene T Wu

(57) ABSTRACT

An invention and method that generate dynamical shaped voltage-gradient geometries through a plurality of dual-modal electrode-contacts placed around the biological tissue in vivo. The geometry of the voltage gradient is optimized through a feedback mechanism from the plurality of dual-modal electrode-contacts that can record electric and magnetic field potentials in the biological tissue. A control controls the waveform signal between sets of electrode-contacts to generate dynamically shaped voltage gradients to modulate a specific set of properties in the biological tissue. A method of analysis for the recorded electric and magnetic field potentials is purposed to optimize the shape of the voltage-gradient geometry through modulation of the waveform signal that is sent through the dual-modal electrode-contacts.

6 Claims, 23 Drawing Sheets

(56) References Cited

OTHER PUBLICATIONS

Choi, E.H., Blasiak, A., Lee, J. and Yang, I.H., 2019. Modulation of neural activity for myelination in the central nervous system. Frontiers in neuroscience, 13, p. 952. [Switzerland] p. 1/2, Paragraphs 1-4, p. 3 Sections "Induction of Myelination by Neural Activity" + Section "Enhancement of Myelination Following Modulation of Neural Activity in Vitro".

Yucel, K., McKinnon, M., Chahal, R. et al. Anterior Cingulate Volumes in Never-Treated Patients with Major Depressive Disorder. Neuropsychopharmacol 33, 3157-3163 (2008). https://doi.org/10.1038/npp.2008.40 [Springer, Germany] p. 1, Section "Introduction" + Section "Discussion" Paragraph 1 and Figure 1.

Yi, D.S., Bertoux, M., Mioshi, E., Hodges, J.R. and Homberger, M., 2013. Fronto-striatal atrophy correlates of neuropsychiatric dysfunction in frontotemporal dementia (FTD) and Alzheimer's disease (AD). Dementia & neuropsychologia, 7, pp. 75-82. [Brazilian Academy of Neurology, Brazil] Section"Introduction" Pagraph 3 and Figure 1.

Morales-Quezada, L., Cosmo, C., Carvalho, S., Leite, J., Castillo-Saavedra, L., Rozisky, J.R. and Fregni, F., 2015. Cognitive effects and autonomic responses to transcranial pulsed current stimulation. Experimental brain research, 233, pp. 701-709. [Springer, Germany] Section "Discussion" Paragraph 4/7 and Figure 3.

Fehér, K.D. and Morishima, Y., 2016. Concurrent electroencephalography recording during transcranial alternating current stimulation (tACS). JoVE (Journal of Visualized Experiments), (107), p. e53527. [United States] Section "introduction" Pagraph 1-2 + Section "Representative Results" Paragraph 1, Section "Discussion" Paragraph 1-5.

Higgs, M.H. and Wilson, C.J., 2019. Frequency-dependent entrainment of striatal fast-spiking interneurons. Journal of neurophysiology, 122(3), pp. 1060-1072. [American Physiological Society, United States] Section "Introduction" Paragraph 1-4.

Vöröslakos, M., Takeuchi, Y., Brinyiczki, K., Zombori, T., Oliva, A., Fernández-Ruiz, A., Kozák, G., Kincses, Z.T., Iványi, B., Buzsáki, G. and Berényi, A., 2018. Direct effects of transcranial electric stimulation on brain circuits in rats and humans. Nature communications, 9(1), p. 483. [Nature Portfolio, U.K.] Section " Introduction" Paragraph 4 + Section "Subcutaneous and transcutaneous electric stimulation in rats" Paragraph 1-2, Section "Focused TES effect by Intersectional Short Pulse stimulation." Paragraph 1 + Section.

Khosla, A., Khandnor, P. and Chand, T., 2020. A comparative analysis of signal processing and classification methods for different applications based on EEG signals. Biocybernetics and Biomedical Engineering, 40(2), pp. 649-690. Section "6. EEG signal processing and analysis" and Figure 2, Table 7, Table 12, Table 14, Table 17 [Elsevier, Poland].

Chu, C.J., Tanaka, N., Diaz, J., Edlow, B.L., Wu, O., Hämäläinen, M., Stufflebeam, S., Cash, S.S. and Kramer, M.A., 2015. EEG functional connectivity is partially predicted by underlying white matter connectivity. Neuroimage, 108, pp. 23-33. [Elsevier, Netherlands] Section "Results : Functional network connectivity partially reflects the underlying structural network".

Thatcher, R.W., North, D. and Biver, C., 2005. EEG and intelligence: relations between EEG coherence, EEG phase delay and power. Clinical neurophysiology, 116(9), pp. 2129-2141 [Elsevier, Netherlands] Section "3.2. Cross-validation of mid range IQ subjects" + Section "3.3. Cross-validation using multivariate regression analyses" + Section "2.6. Validation by multiple regression analyses".

* cited by examiner

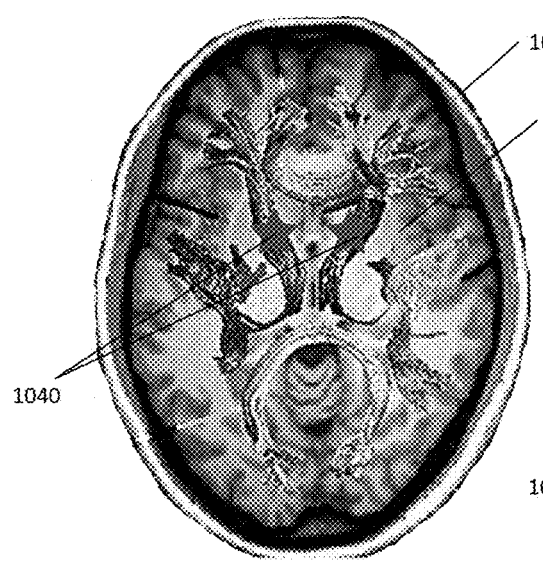
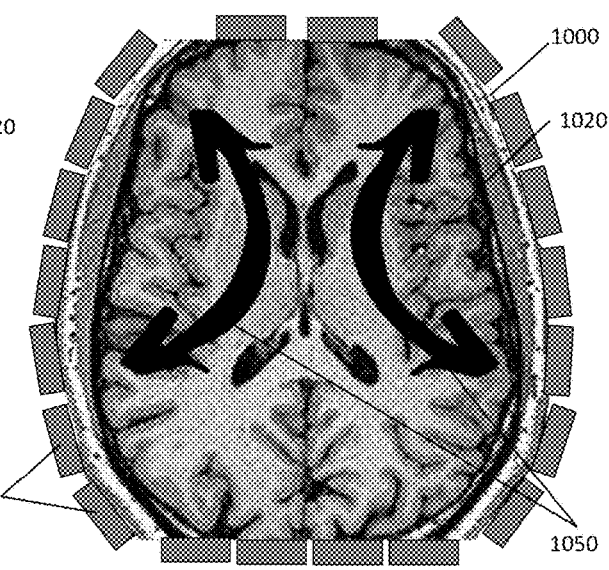
FIG. 1A  FIG. 1B

GENERATING VOLTAGE-GRADIENT GEOMETRIES IN BIOLOGICAL TISSUE

CROSS-REFERENCE TO RELATED APPLICATIONS

This patent application claims priority to Provisional Patent Application No. 63/288,649 filed Dec. 13, 2021, entitled "GENERATING VOLTAGE-GRADIENT GEOMETRIES IN BIOLOGICAL TISSUE AND WET MEDIA."

INCORPORATION BY REFERENCE

All publications, including patents and patent applications, mentioned in this specification are herein incorporated by reference in their entirety to the same extent as if each individual publication was specifically and individually cited to be incorporated by reference. This includes patent application US 17/336,224.

FIELD OF THE INVENTION

Described herein are systems and methods for using voltage-gradient geometries for tissue modulation including modulation in the central nervous system.

BACKGROUND OF THE INVENTION

Arousal and sleep represent fundamental physiological domains, and alterations in the form of insomnia (difficulty falling or staying asleep) or hypersomnia (increased propensity for falling asleep or increased sleep duration) are prevalent clinical problems that can lead to the progression of neurodegenerative disorders; most notably, Dementia and Alzheimer's Disease. Studies have shown that people who slept six hours or less per night in their 50s and 60s were more likely to develop dementia later in life. The findings suggest that inadequate sleep duration could increase dementia risk and emphasize the importance of good sleep habits.

Many physiological signatures can be measures and correlated in sleep with Dementia and Alzheimer's Disease including abnormalities in connectivity between parts of the brain (most importantly frontal-striatal circuits), low fractional anisotropy values of distinct tracts in the brain with termination points between neocortical and subcortical regions leading to abnormal regulation of homeostatic activities (including lower heart hart variability, increased cortisol levels, increased sensitivity to physical stimuli leading to pain/fatigue, and weight issues), reduction white matter integrity (a value reflected by comparison between healthy and non-healthy brain) in and across regions of the brain correlated with affect and emotional modulation/awareness, increased lateralization of frontal lobe activity as characterized by interhemispheric decoherence on electroencephalogram (EEG) recordings, and low density EEG recordings on physiological level most specifically recorded across the frontal lobe with theta-band activity, and/or lower hippocampal volume identified through functional magnetic resonance imaging (fMR) thus indicated a lack of proliferation of progenitor stem cells defined as neurogenesis.

Recording, analyzing, and correlating specific neuroimaging biomarkers to different noninvasive neuromodulation stimulation parameters is the foundation of precision neuromodulation. The content herein discusses the details of precision neuromodulation during sleep for both medical, specific to Dementia and Alzheimer's Disease and consumer applications.

FRONTAL-STRIATAL CIRCUIT

The frontal lobe region has been extensively studied in the pathophysiology of neurodegenerative disorders due to its vast connection to emotional subcortical regions through distinct branches of frontal-striatal circuit connections. The striatum is a region in the basal ganglia with high importance in information processing and executive functions with the frontal lobe. Abnormalities within this circuit are often involved in various neurodegenerative disorders such as Alzheimer's disease and Parkinson's Disease and neuropsychiatric disorders including, but not limited to: Major Depressive Disorder, Schizophrenia, Obsessive-Compulsive Disorder, Attention Deficit Hyperactive Disorder, and Manic-Depressive Disorder. Furthermore, with patients suffering from poor sleep quality, the degree of disruption in the frontal-striatal circuits as measured through graph theoretical analysis is linked to the severity of insomnia.

There are two leading theories on the role of the frontal-striatal circuit and its association with neurodegenerative and emotional disorders. The first is the action selection theory which suggests the frontal cortex chooses multiple possible next actions to generate based on environmental stimulation and the striatum choose a single of those actions to carry out by inhibiting the others and sending the chosen action to cerebral regions to carry out a movement and indirectly modulating internal body states. The second theory is reinforcement learning suggests that the selection of actions is guided by the reward expectation of a given decision inputted from the frontal cortex. Thus, abnormalities between the frontal cortex and the striatum connections lead to negative self-esteem as positive actions and inability to formulate decisions which leads during the striatal selection process when integrating information from the frontal cortex.

The frontal-striatal circuit passes through distinct regions, also considered to be part of the pathophysiology of the neurodegenerative disorders mention above, to one important region in the frontal cortex named the dorsolateral prefrontal cortex. The regions that the frontal-striatal circuit passes through include, but not limited to: the anterior cingulate cortex, the subcallosal cingulate, and fibers along with the forceps minor. The anterior cingulate cortex (ACC) plays many functions including modulating higher-level functions such as empathy, morality, decision making, and attention, and automatic function such as blood pressure and heart rate. It sits between the frontal lobe and the limbic system. Abnormal activation of ACC (indicated by increased metabolic activity on fMRI imaging), a reflection of reduced white matter integrity, is correlated with enhanced rumination of social event/environmental stimuli leading to a disruption in the decision-making process carried out by the striatum is highly exhibited in individuals suffering from dysfunctional sleep symptoms. A restoration of white matter volume in the ACC, and thus integrity, from electroconvulsive stimulation, increased the prediction that the patient with a mood disorder receiving the treatment shall respond to the therapy.

Although research on the mechanism of action to restore white matter volume in its infancy, Hebbian theory tells us claims that an increase in repeated synaptic activity, thus meaning the frequent depolarization and transmission of a neuronal impulse from a presynaptic cell through electrical or chemical messengers onto a postsynaptic cell, leads to synaptic strengthening by the myelination of the axonal branches of the associated depolarizing neuron. Hence, controlled increases in neuronal activity emerging from internal brain activity or external neurostimulation devices lead to increases in myelination, long-term potentiation, and plasticity in a given region.

The frontal-striatal circuit also involves a region of the brain named the subcallosal cingulate (SCC) or otherwise known as Brodmann's Area 25. It has been extensively studied as a deep brain stimulation site for the treatment of Major Depressive Disorder with dysfunctional sleep patterns to its involvement in the frontal-striatal circuit as well the fiber bundles pass through the region such as the cingulum bundle, forceps minor, and the uncinate fasciculus. Like the ACC, abnormal increased metabolic activity in the SCC is frequent in patients with treatment-resistant depression with dysfunctional sleep symptoms. High-Frequency deep brain stimulation on SCC leads to an alleviation of symptoms in patients with treatment-resistant depression with dysfunctional sleep symptoms further increasing the importance of frontal-striatal connections and their association with mood disorders.

The Forceps Minor emerges from the anterior portion of the corpus callosum, passing through various parts of the cerebral cortex, such as SCC, and contains fibers moving backward through the ACC, along with anterior thalamic projections, stopping at many endpoints, of which include regions in the striatum and thalamus. Its extension into each hemisphere of the frontal lobe serves as an attention control mediator. Reduced fractional anisotropy (a scalar value between 0 and 1 that describes the degree of anisotropy, or directional dependency, of a diffusion process) of the forceps minor is correlated with dysfunctional sleep and attention symptoms.

The Fractional Anisotropy (FA) is a value deduced from a specific analysis of MRI images to observe the predicted diffusion of water in the brain to assist with the mapping of white matter tracts, such as the forceps minor. FA is also indirectly correlated with the physical properties of axonal fibers such as myelination, degree of axonal branching, and volume of cerebral spinal fluid around the measured region of interest. Low FA values, near 0, indicate unrestricted diffusion equally across all 3 spatial dimensions and high FA values, near 1, indicate diffusion restricted on 1 axis across the 3 spatially dimensions. The concept that underlies this phenomenon is that increased myelination of tracts will have high FA values due to the controlled, restricted, and fast propagation of signals from the beginning and to the end of the tract without chaotically diffusing to regions around the tract. Reduced FA is frequently observed in patients suffering from dysfunctional sleep symptoms in the forceps minor, uncincate fasciculus (connecting areas in the brain stem to the frontal lobe), cingulum bundle (connecting frontal lobe to occipital lobe and hippocampal areas), anterior thalamic radiations, and the superior longitude fasciculus (connecting frontal, temporal, and parietal lobes). The areas mentioned play crucial roles in sustaining high-level activity, attention, mood regulation, and homeostatic functions. Abnormalities within these areas are often involved in various neurodegenerative disorders such as Alzheimer's disease and Parkinson's Disease and neuropsychiatric disorders including, but not limited to: Major Depressive Disorder, Schizophrenia, Obsessive-Compulsive Disorder, Attention Deficit Hyperactive Disorder, and Manic-Depressive Disorder.

Many structural and functional neuroimaging studies have observed widespread dysfunctions in the frontal-striatal-limbic-thalamic regions in patients suffering from Alzheimer's disease and patients with dysfunctional sleep symptoms. Furthermore, it has been found that patients suffering from dysfunctional sleep patterns experience hypoactivation in the inferior frontal cortex as well as decreased activations in the thalamic regions; the frontal striatal circuit connections the inferior frontal cortex with deep thalamic regions. Thus, it has been concluded that the frontal-based circuits and striatal-based systems play an essential role in the pathogenesis and neurobiological underpinnings of neurodegenerative disorders and dysfunctional sleep disorders.

NEURODEGENERATIVE DISORDERS, FRONTAL CORTEX, AUTOMATIC NERVOUS SYSTEM, AND SLEEP DYSFUCTION

Homeostatic disruption and Automatic Nervous System (ANS) Dysfunction can subjugate an individual to a neurodegenerative disorder with abnormal sleeping patterns symptoms. Major markers of ANS dysfunctions correlated with mood disorders include abnormal heart variability, increased cortisol levels, abnormal weight fluctuations, increased chronic pain, increased fatigue, higher body temperature, high blood glucose levels, iron deficiency, and elevations in calcium levels.

Heart Rate Variability HRV is an indicator for dysfunctional sleep patterns from a large body of research. Low levels of HRV characterize emotional dysregulation, decreased psychological flexibility in social interaction (also indicated by Frontal-Striatal circuit disruptions) which in turn leads to low metabolic activity in the frontal lobe otherwise known and hypo-frontality (a neurological signature for sleep dysfunctional patients). Studies show that HRV is a promising biomarker to determine the prefrontal cortex efficacy in modulating emotional reactivity, social engagement, and psychological flexibility. In the central nervous system, the frontal cortex has projections through the amygdala to sympathoexcitatory, cardioacceleratory subcortical circuits that control heart rate variability. Under stress conditions, specific areas of the frontal cortex become underactive which implies less modulation of sympathoexcitatory subcortical circuits leading to lower HRV. Furthermore, there is evidence of a positive relationship between the amplitude of heartbeat modulations and the level of activation of the frontal cortex. The medial prefrontal cortex learns slowing or increasing in heart rate when experiencing learned or new stimuli. This indicates the necessity of the frontal cortex integrity in responding to environmental stimuli and its association with heart rate variability suggesting the frontal lobe activation is critical to neurodegenerative, sleep, and mood disorders on a cortical and cardiac level.

People with dysfunctional sleep symptoms, like insomnia, and neurodegenerative disorders tend to have elevated levels of cortisol in their bloodstream and reduced levels of serotonin in their brains which can lead to high blood pressure, high blood sugar, weakened immune system and increased fat storage. On the central nervous system level, elevated cortisol levels impair top-down executive control coming from the prefrontal cortex onto limbic regions, which include the striatum. Also, the working memory performance is reduced with elevated cortisol leading to smaller hippocampal volumes and reduced activity in the Dorsolateral Prefrontal Cortex. Negative correlations between cortisol levels and cortical thickness in areas in areas like the left dorsolateral prefrontal cortex, ventral prefrontal regions, right dorsolateral prefrontal cortex, and medial orbital frontal cortex. Increasing frontal cortex thickness through non-invasive stimulation methods has been shown to reduce cortisol levels in individuals A key characteristic of appetite changes such as weight gain or weight loss is exhibited in individuals with dysfunctional sleep patterns. Some individuals force themselves to eat while others gain weight faster than typical. It has been revealed that reduced inferior frontal gyrus functional connectivity in patients suffering from eating disorders. This alerted integrity in the frontal cortex leads to hyperactivity of appetite changes in mood disorders. Dietary self-regulation is dependent upon the ability of the prefrontal cortex to exert control of food choices which increases with structural and functional integrity.

WHITE AND GRAY MATTER, NEURODEGENERATIVE DISORDERS, AND DYSFUNCTIONAL SLEEP PATTERNS

Widespread structural abnormalities have been reported including regional tissue loss in the hippocampus, amygdala, basal ganglia, prefrontal cortex, and anterior cingulate cortex. These results suggested that a dysfunctional cortical-subcortical neural circuit is involved in the pathophysiology and psychopathology of Dementia and Alzheimer's Disease. Investigations of white matter have become a rapidly growing interest in the investigation of neurodegenerative disorders and dysfunctional sleep symptoms. Reduced white matter fractional anisotropy was measured in the genu of the corpus callosum. The corpus callosum (CC) is the largest white matter tract that connects the two hemispheres of the brain, and the genu of the CC is contained in the rostral region, near to the prefrontal cortex. Patients with a disruption in axonal myelination exhibit executive deficits as well as cognitive dysfunction.

The cingulum bundle lies in the cingulum gyrus, right above the corpus callosum, which helps connect prefrontal regions with para-hippocampal regions. Reductions in fractional anisotropy were reported in this region in treatment-resistant depression with dysfunctional sleep symptoms. Due to the prefrontal-hippocampal connections through the cingulum bundle, it has been shown that disruptions in this region lead to memory deficits and difficulty for the default mode network to renormalize. This means baseline brain activity is alerted in comparison to controls leading to changes in episodic memory formation and retrieval. There is also an inverse relationship between FA levels in the Cingulum bundle and anhedonia (inability to feel pleasure) which is common for patients suffering from dysfunctional sleep patterns. The Cingulum bundle is connected to the frontal cortex through the subcallosal cingulate and forceps minor.

Psychomotor retardation involves a slowing down of thought and reduction in physical movements in an individual exhibited in neurodegenerative disorders. Structure alterations in white matter pathways between the dorsolateral prefrontal cortex and the supplemental motor area are correlated with psychomotor retardation. Modulating dorsolateral prefrontal cortex activity with noninvasive brain stimulation may improve psychomotor retardation in neurodegenerative disorders. Repetitive transcranial magnetic stimulation (rTMS) applied to the dorsolateral prefrontal cortex has been proposed as an alternative, effective, and safe therapeutic strategy for neurodegenerative disorders and psychomotor symptoms related.

Furthermore, it has shown that lower gray matter volume in the bilateral dorsolateral prefrontal cortex, including parts of right and left inferior and middle frontal gyri, right frontal polar cortex, and bilateral thalamus among other areas. There has been conflicting data about whether or not transcranial stimulation of any sort induces gray matter changes under the stimulated region of interest. However, there is conclusive evidence that transcranial magnetic stimulation causes morphological changes to the region of stimulation. Reversal of gray matter deficits in the frontal cortex and anterior cingulate cortex has been observed after a course of TMS treatment.

Lastly, it has been shown that the gray matter volume (GMV) in the left orbitofrontal cortex (OFC) is lower in patients suffering from neurodegenerative disorders with dysfunctional sleep patterns. There has also shown a negative relationship between gray matter density in the left OFC and earlier morning awakenings; a common pattern in patients suffering from dysfunctional sleep symptoms. Moreover, there is reduced GMV in the bilateral OFC and adjacent bilateral inferior frontal gyrus (IFG) pars orbitalis in patients with the fragmentation of sleep. This leads to a decreased integrity of white matter tracts in the frontal lobe and anterior internal capsule as demonstrated with diffusion tensor imaging.

ELECTROENCEPHALOGRAM AND STRUCTURAL/FUNCTIONAL ACTIVITY OF FRONTAL CORTEX IN SUBJECTS WITH NEURODEGENERATIVE AND DYSFUNCTIONAL SLEEP SYMPTOMS

White matter diseases and abnormalities also have an influence on electroencephalogram (EEG) oscillatory behaviors. EEG provides brain activity on fast, millisecond time scales which is strongly influenced by white matter axons. There are many computer methods to provide models of the brain's surface at roughly the 2-3 cm scale. The relationships between gray and white matter structure and connectivity are responsible for the dynamic behavior of the brain and recording measurements made with EEG; any impairment made to this complex system as a result of a neurological disorder can be elucidated from EEG measurements.

There is an important relationship between alpha and theta bands and axon propagation. Myelinated axons (white matter) control action potential speed and the synchrony of long distant regions which is very important in maintaining the stability of executive functions including mental performance, learning, memory acquisition and recall, and mood regulation. A broad range of psychiatric disorders, including schizophrenia, chronic depression, bipolar disorder, obsessive-compulsive disorder, and posttraumatic stress disorder, has recently been associated with white matter defects, as have neurodevelopmental cognitive and emotional disorders including autism, dyslexia, and attention-deficit hyperactivity disorder. The correlation of firing in time of synapses of neighboring neurons is associated with increase synaptic plasticity due to their strengthened connections between each other. This correlation, when sustained, is resulted from an increase in spectral density within the EEG electrodes lying on the frontal lobe due to the larger transmembrane voltage in that region when both neurons fire and summate simultaneously. The voltage changes in a neuron last for about 2-4 milliseconds, thus able to be recorded by EEG devices.

Propagation speed, which plays a role in whether or not a collection of neighboring neurons is firing together or not, varies widely among areas of the brain as well as different types of neurons. The Corpus Callosum is unmyelinated at birth, meaning slow propagation speeds between neurons, which results in a 150-300 millisecond propagation time when unmyelinated and 30 milliseconds when myelinated. When regions such as CC are defected due to a neurological or psychiatric disorder, interhemispheric talk and coherence are also affected. Interhemispheric coherence is highly exhibited in healthy adults and lacking in patients suffering from neurodegenerative disorders. Interhemispheric coherence helps scientists measure whether or not distant networks in opposite hemispheres, such as bilateral regions in the frontal cortex, are functionally integrated.

The structural and functional connectivity of the brain is often represented on graph networks. When the brain is interpreted as a complex graph of nodes and edges (neurons and axon connections), imaging data can be interpreted as the strength between local or non-local nodes on the graph on a spatiotemporal scale. Sources of nodes with high strength can be seen as EEG recordings that are in phase with one another but can be with different magnitudes. Patients with neurodegenerative disorders show a lack of functional connectivity between distant regions in the frontal-temporal, parietal-occipital, and, most importantly, between hemispheres of the frontal cortex.

Based on histological analysis, myelination between the prefrontal cortex to the hippocampus, although beginning prenatally, continues through childhood and beyond. Over time, there is increased synchronization between cortical and hippocampal areas and a disruption in the development of myelinated pathways during childhood brain development can lead to a desynchronization between these two areas resulting in neurological and psychological deficits continuing to adulthood. This disruption of myelination during the developmental phase between subcortical and cortical networks destroys the overall coherence of brain rhythms between areas and slows down in cognitive processes known as dysrhythmia. Thalamocortical dysrhythmia is associated with dysfunctional sleep disorders, schizophrenia, obsessive-compulsive disorder, and depressive disorder and the natural oscillation frequencies in the prefrontal cortex are slower in individuals with schizophrenia and depressive disorder.

There is direct evidence showing noninvasive stimulation having a direct influence on EEG signals both during and after stimulation. Transcranial Current Stimulation Modulates the resting membrane potential in a polarity-dependent fashion and, as such, increases the sensitivity for neurons in a given region to hyperpolarize or depolarize depending upon the electrode polarity being positive or negative (cathode or anode respectively). Therefore, traditional direct current stimulation (tDCS) where the polarity does not change over time may cause EEG imbalances if tDCS were placed on the hemispheres of the frontal cortex. This may be advantageous in some circumstances where one needs to reduce activity in certain superficial regions, as in the case of epilepsy, but not in psychiatric conditions such as depression or anxiety, where there is an overall lower amount of activity. Long-term effects of stimulation depend upon Long Term Potentiation and Long-Term Depression Mechanisms mediated by NMDA Glutaminergic Receptors or automatic GABAnergic activity and intracellular calcium levels concentration.

The application of transcranial stimulation also affects downstream structures, not only in the region of stimulation. In mice, it was shown that transcranial stimulation of the frontal cortex enhanced neural activity in the nucleus-accumbens. Furthermore, it has been shown that ipsilateral (one-sided) stimulation leads to axonal and dendritic growth in both hemispheres. This, in turn, will lead to higher levels of interhemispheric coherence on EEG scans.

ELECTROENCEPHALOGRAM COHERENCE AND NONINVASIVE STIMULATION

EEG coherence is an important concept to address the functional integration or segregation between two regions over time and is important for assessing how and if the brain is driving cognitive function and behavior. Coherence is a value ranging from 0 to 1 that measures the degree to which two or more EEG signals rise and fall together over some time. If the two signals rise and fall together often, it suggests functional connectivity. The Coherence of a signal depends upon the EEG power spectra which are obtained through a discrete Fourier Transform that takes signals from the time domain to the frequency domain.

As stated, the functional networks in the frontal cortex in patients with psychological and neurological diseases are abnormal due to a variety of environmental and physiological factors as well as the connectivity of those networks to subcortical areas. Increasing the level of coherence shows cross hemisphere connectivity which is indicated by increases in white matter density and fractional anisotropy in the forceps minor, anterior cingulate cortex, bihemispheric dorsolateral prefrontal cortex, and corpus callosum to name a few. A noninvasive brain stimulation paradigm, such as TMS, ECT, tCS that can induce the positive physiological change in terms of white matter density in the frontal cortex as such will increase the levels of coherence between the hemispheres in the frontal cortex to alleviate patient symptoms in both neurological and psychological diseases.

Repetitive Transcranial Magnetic Stimulation (rTMS) can enhance the connections between the stimulated area and non-stimulated regions and these effects are sustained for several minutes. In a paper titled "Observation of EEG coherence after repetitive transcranial magnetic stimulation", 19 healthy subjects received biphasic sine wave pulses through a figure-eight shaped flat coil with the rise period of the pulse being 60 Microseconds, the pulse duration being 250 Microseconds, and magnetic field strength of 2 Tesla. Two trains over the left motor cortex, in the frontal lobe, were delivered at an interval of 5 minutes and each train contained 30 pulses at 10 Hz. 14 EEG channels were collected over the frontal, temporal, and parietal area. After stimulation, F3 (electrode in the left frontal cortex) showed increased coherence with other regions. More specifically, the values in the low-frequency range decreased by 7.6% while the values increased in the alpha (1.5%), beta (5.4%), and gamma (4.8%) bands. These higher frequencies are indicative of greater functional connectivity than lower frequencies.

Transcranial Alternating Current Stimulation (tACS) also has been shown to modulate endogenous brain activity in a frequency-dependent manner. By applying a weak alternating current to the scalp, tACS can entrain natural neural oscillations in the range of the stimulation frequency. In comparison to a sham group, a study showed that participants receiving stimulation at their alpha frequency showed increased alpha power and coherence between hemispheres. It is important to note that the frequency of the tACS being applied is correlated to the frequency it entrains over the regions in which the electric field passes. For example, 10 Hz tACS showed better alleviation of depressive and sleep symptoms than 40 Hz tACS when electrodes were positioned over the frontal cortex. A downside of tACS is that it does not provide a sufficient level of current to depolarize neurons to efficiently induce myelination of axonal branches and increase functional connectivity between regions to induce greater interhemispheric coherence. In summary, tACS is a tool to entrain brain oscillations without directly affecting neural circuits.

New data is showing that the ability to multiplex current in the brain without sending higher levels of current just be sending the current faster than the time integrity constant of the neuron. The time integrity constant of the neuron is 1-100 milliseconds and if an electric charge pulse is sent several times before that constant, the charge pulses will be summated relative to the neuron. Meaning, one can induce depolarization without excess current simply by increasing the frequency of the pulse. The pulses, however, must be of the same polarity for the current to summate. Otherwise, the current will negate and have 0 effects on the neurons. Thus, it makes sense that a new paradigm, named, transcranial pulsed current stimulation (tPCS) has emerged recently. It is a non-invasive stimulation paradigm similar to tDCS and tACS expect the current is being sent in discrete pulses. So far, tPCS used pulses with a frequency of 1 to 5 Hz. Although showing more effective results than tACS and tDCS in modulating brain connectivity, it is still limited in providing a sufficient size voltage/area in the brain to affect spike activity as explained in the next paragraph.

In the paper "Direct effects of transcranial electric stimulation on brain circuits in rats and humans," DOI: 10.1038/s41467-018-02928-3, by Vöröslakos, et al, it was quoted "The effectiveness of currently used TES protocols on local neuronal networks is a subject of extensive debate. At least two factors contribute to this controversy. First, the large electric fields induced by alternating current TES (transcranial alternating current stimulation; tACS) often prevent simultaneous measurement of electric (electroencephalographic, EEG), magnetic (magnetoencephalographic, MEG), or imaging (blood-oxygen-level-dependent, BOLD) signals. Recent experiments attempted to alleviate the amplifier saturation problem and remove the stimulus artifacts. However, in those experiments, the expected brain rhythm entrainment was examined at the same frequency of the applied TES (e.g., 10 Hz tACS induced increased power in the alpha band), raising the possibility that large tACS artifacts which are several thousand-fold larger than the scalp signal, or a harmonic of the artifact, have contaminated the results. A second indirect approach takes the voltage gradients shown experimentally to produce spike entrainment and estimates the corresponding current intensity applied at the scalp surface. However, translation of results obtained from models, in vitro observations, and experiments performed on experimental animals to humans is complicated by an incomplete understanding of how skin, subcutaneous soft tissue, skull, cerebrospinal fluid, and brain folding affects current spread. While strong stimulation (>50 mA; 0.5 ms pulses) delivered through intracranial screw electrodes in anesthetized patients have shown convincing brain network-induced effects, the current intensity applied to the scalp needed to acutely affect neuronal patterns is yet to be established." And, as it was stated later in the paper, "Our direct measurements and indirect estimation provided concordant results and established that in humans at least 4-6 mA currents should be applied by conventional tACS electrodes to reliably and instantaneously affect neuronal circuits." It was further shown in the paper that 4-6 mA induced a voltage gradient of at least 1 mV/mm and that this is the minimum voltage/area needed to affect spiking activity. Stronger activity is needed to affect network oscillations. To note, in rodents and human cadaver brains, ~75% of scalp-applied currents are attenuated by soft tissue and skull. This means that an average of 1-1.5 mA when entering the brain itself, after passing the soft tissue and skull, when 4-6 mA is applied at the surface. This will generate a voltage gradient of 1-1.5 mV/mm.

It is cited that at least a 1 mV/mm voltage gradient is needed to affect neuronal spiking. Since the electrodes on the device are placed on the outside of the head, noninvasively, the current will be attenuated by the skin and skull by roughly 75-80%. Therefore, 4-6 mA must be passed through the brain to induce a 1 mV/mm voltage gradient in a specific region of interest. One can induce a 1 mV/mm voltage gradient by multiplexing current faster than the time integrity constant of the neuron being 1-100 milliseconds. Better explained, one can send multiple pulses of smaller current levels to add up their voltage gradient before the neuron can respond to the voltage gradient. This can trick the neurons into responding to stimuli that are larger than what is sent in. The time integrity constant of the neuron is the time it takes for the neuron to respond to outside stimuli, such as an electric or magnetic field. Meaning, one can summate electric fields to illicit a higher voltage gradient while keeping the current on the skin low such that the neuron will respond to the total summated current sent in the 1-100 mS. Summating the electric fields to achieve higher voltage gradients is necessary to induce depolarizations of the neurons within the voltage gradient. This allows for neurons to respond to a sufficient external stimulus to induce depolarization while maintaining skin safety. So far, no one has figured out a transcranial device with the optimal pulse sequences to elicit sufficient depolarization, interhemispheric coherence, and induce brain network effects.

Inducing larger voltage gradients in the brain can have local, meso, and global effects in network connectivity which in turn leads to more topological intact frontal-striatal circuits. In neurodegenerative disorders, repetitive stimulation of the frontal cortex leads to increased FA values in frontal-striatal circuits which in turn reduces dysfunctional sleep patterns exhibited by the patient as detected and analyzed through fMRI. This increase in frontal lobe metabolic activity elicited through higher voltage gradients reverse sleep deprivation symptoms as patients suffering from sleep dysfunctionality have abnormal metabolic activity in the frontal cortex which is modulated through frontal-striatal circuits. During sleep, the flow of cerebrospinal fluid in the brain increases dramatically, washing away harmful waste proteins that build up between brain cells during waking hours. A new study links sleep-dependent brain activity with the excretion of toxic proteins related to Alzheimer's Disease. Thus, the facilitation of deep sleep through noninvasive stimulation at night can increase the excretion of toxic proteins and reduce plaque formation through the glymphatic system related to neurodegenerative disorders.

Furthermore, it has been supported that the white matter network architecture guides the propagation of direct-electrical-stimulation voltage gradients. Several in silico brain models have been developed that prioritize the shape, orientation, and position of the voltage-gradient being generated in parallel with the shape, orientation, and position of the neuronal tract that the voltage gradient is propagating upon. In that, the more closely oriented the voltage gradient is to a neuronal tract, the better the voltage gradient can excite, inhibit, and/or induce a physiological, biological, and/or mechanical response to the organism on a microlevel, mesolevel, and macrolevel. Due to the variability in tract shapes and geometry both in vivo and in vitro, one would need to create specifically shaped voltage-gradient geometries to optimize the excitation or inhibition of electrical signal in that tissue to achieve a certain function on a physiological, biological, and/or mechanical level.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 1B shows a 2-dimensional perspective view of a voltage gradient generated across the Thalamic Radiations shown in FIG. 1A in the brain.

DESCRIPTION OF THE INVENTION

Figure 9:
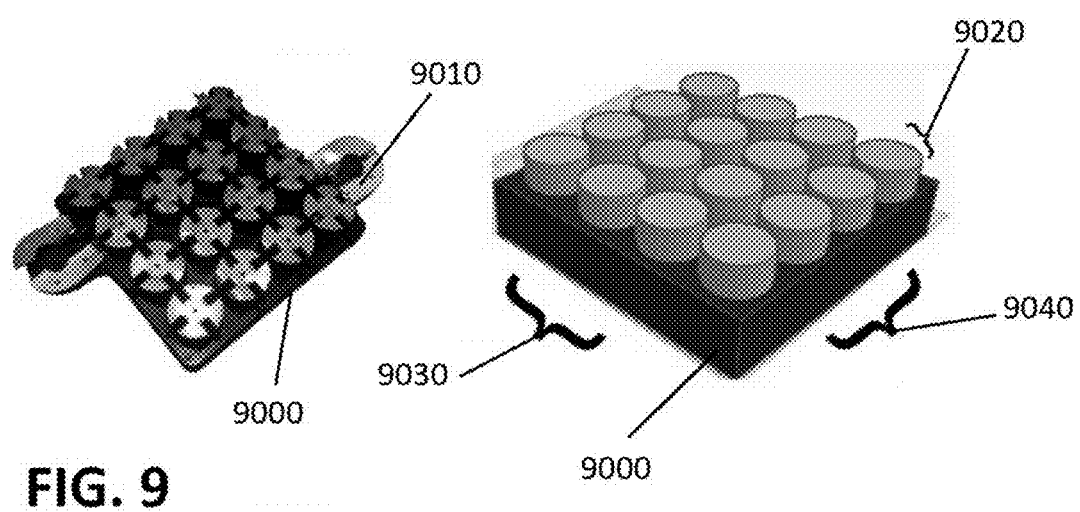
FIG. 9 is a 3-Dimensional photograph and representation of an electrode with sub-electrode groups.

In the embodiments herein, the electrode-contacts can be dual functioned in which the sub-electrodes can generate different shaped voltage-gradient geometries through the modulation of waveform parameters into biological tissue, in vitro, and in vivo, and can record voltage-gradient potentials in underlying electrical or magnetic activity in those biological tissues. In the embodiments herein, the electrode-contacts can be dual functioned in which the sub-electrodes can generate different shaped voltage-gradient geometries through the modulation of waveform parameters into biological tissues, in vitro, and in vivo, and can record voltage-gradient potentials in underlying electrical or magnetic activity in those biological tissues. FIG. 9 depicts an example electrode-contact 9000 with electrical interface 9010 with sub-electrode-contacts 9020 and variable-width 9030 and depth to the electrode-contact 9040. In the attached figure, each electrode-contact has 16 sub-electrode-contacts. Each sub-electrode-contact operates in a sub-electrode-contact group. For example, a device can have four sub-electrode-contact groups, however, any number of sub-electrode-contact groups can be introduced. For Line V1, each sub-electrode-contact group will correspond to the electrode-contact the 16 sub-electrode-contacts are contained within. Thus, each electrode-contact contains each of the four sub-electrode-contact groups which contain 16 sub-electrode-contacts each. Each sub-electrode-contacts group can operate with another sub-electrode-contact group in a sub-electrode-contact super-group (SESG). A SESG can contain between 1-3 sub-electrode-contact groups or 1−(n−1) where n=# of sub-electrode-contact groups. Thus, there are (n−1) possible sized SESG (1,2, or 3 sub-electrode-contact groups. Each SESG can be combined in a sub-electrode-contact super-group network (SESGN). The combinations of SESGN include all possible sized SESGs, meaning, in a 4 sub-electrode-contact device, 2,3, or all 4 sub-electrode-contacts can be on during stimulation. As such, there is a total of 50 different combinations of SESG that can be combined in a SESGN with 4 sub-electrode-contact groups. The algorithm to determine the number of different SESG combinations of size n is: $a(n)=3^{\wedge}(n-1)-2*2^{\wedge}(n-1)+1$ (Stirling numbers of the second kind). Electrode-contacts and sub-electrode-contacts can be made from a wide variety of conductive materials and flexible circuits to account for different head topologies. Furthermore, a controller modulates the firing, switching, grouping, grounding, and deactivating of sub-electrode-contacts at rates of 0 Hz to 100 kHz selected during the predetermined time. Moreover, electrical and/or magnetic pulses are me modulated from the control at a rate of 0 Hz to 100 kHz to send pulses faster than the membrane potential of the neuron (1-100 ms). All electrode-contacts and sub-electrode-contacts in a sub-electrode-contact network can modulate the shape, orientation, and position of voltage-gradient geometries to enhance and/or inhibit a specific physiological, biological, and/or mechanical response.

The most suitable materials to develop the electrodes are silver chloride, silver, gold, stainless steel, or another metal compound that can conduct electricity with low-temperature sensitivity. Electrode dimensions/number and sub-electrode-contact dimensions/number are not exclusive, other dimensions/numbers can be implemented based on the purpose of the embodiments, systems, processes, and methods.

Identifying specific tracts and bundles in the brain can allow physicians and practitioners to generate novel voltage-gradient geometries across neuronal structures to precisely modulate networks in the brain through a dispersed electrode array around the skull. This leads to a cascade of microlevel, mesolevel, and macrolevel responses that cannot be achieved through traditional stimulation. In FIGS. 1A, 2A, 3A, 4A, 5A, and 6A, we identify the major tract pathways in the cortex on which generative novel voltage-gradient geometries, measured by mV/mm, will lead to positive effects for different brain states in neurodegenerative, neuropsychiatric, and neuromuscular disorders as well as brain states in healthy individuals carrying-out active or passive tasks (meditation, exercise, cognitive activity, sleeping, etc.). It should be noted that any voltage gradient with a new potential above 200 mV/mm can lead to adverse events as defined by the Food and Drug Administration (FDA); all generation of voltage-gradient geometries shall be bounded underneath a net potential 200 mV/mm. In FIG. 1A, the bilateral thalamic radiations 1040 connect subcortical emotional centers to frontal lobe regions for higher cognitive processes. Generating a voltage gradient 1020 in FIG. 1B with a specific geometry from a distributed network of noninvasive electrodes 1030 shown in FIG. 1B allows the activation of microlevel, mesolevel, and macrolevel processes that reside and emerge from these radiations. The most notable effects induced from voltage gradients are the induction sub-threshold, at-threshold, and supra-threshold action potentials. Actions potential inductions by voltage gradients with specific geometries are due in part to the capacitive properties of neurons; neurons have a time integrations constant that ranges from 1-100 ms which allow voltage gradients with specific parameters (pulsed, chaotic, high frequency, etc.) to create a large electric charge surrounding the neuron through capacitive charge integration without increasing the current levels from the electrode site. All voltage-gradient geometries in FIGS. 1B, 2B, 3B, 4B, 5B, and 6B are depicted in a 2-dimensional form.

Figure 10:
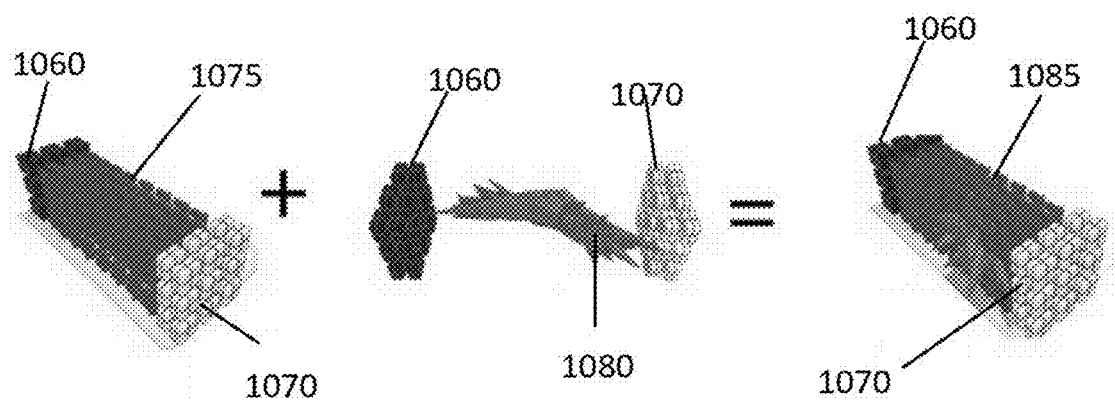
FIG. 10 is a 3-dimensional perspective view of a neuronal tract within a voltage gradient.

There are several neuronal tracts in the central nervous system that connect different networks; being able to optimize the geometry of the voltage gradient generated to adapt its shape to the tract itself through a specific feedback mechanism is a novel invention and method in the field of neuroscience. Generating different voltage-gradient geometries along specific tracts are pictured in FIGS. 1A, 1B, 2A, 2B, 3A, 3B, 4A, 4B, 5A, 5B, 6A, and 6B. Each of FIGS. 1A, 1B, 2A, 2B, 3A, 3B, 4A, 4B, 5A, 5B, 6A, and 6B contain a skull 1000, brain tissue 1020, and non-invasive electrical-stimulation electrodes, 1030 in contact with the skull. Tracts include, but are not limited to, Thalamic Radiation 1040 in FIG. 1A, Interhemispheric Thalamic Radiations 2040 in FIG. 2A, Forceps Minor 3040 in FIG. 3A, Superior Longitudinal Fasciculus 4040 in FIG. 4A, Interhemispheric Superior Longitudinal Fasciculus 5040 in FIG. 5A, and Forceps Major 6040_in FIG. 6A. The corresponding voltage-gradient geometries are pictured on 1050 in FIG. 1B, 2050 in FIG. 2B, 3050_in FIG. 3B, 4050 in FIG. 4B, 5050, in FIG. 5B and 6050 in FIG. 6B. As stated, there are several neuronal and biological tracts in the central and peripheral nervous system with various corresponding voltage-gradient geometries that can be delivered on. FIG. 10 shows a 3-dimensional view of how a neuronal tract 1080 is visualized and combined with a voltage-gradient 1075 between cathode electrode 1060 and anode electrode 1070 resulting in voltage gradient-tract interaction 1085.

Figures 2A, 2B:
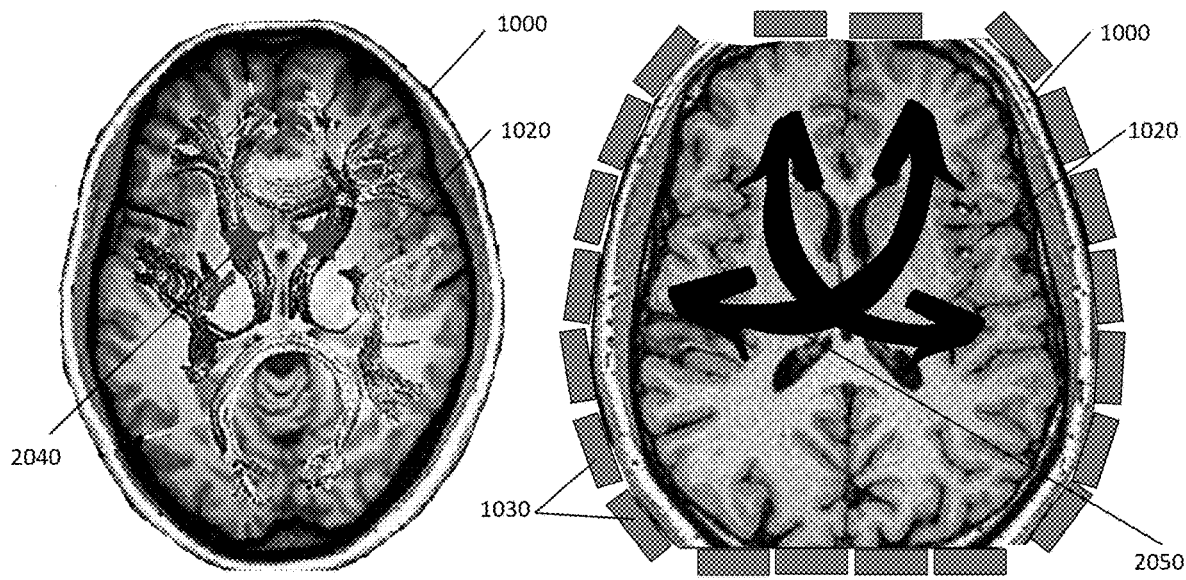
FIG. 2B shows a 2-dimensional perspective view of a voltage gradient generated across the Interhemispheric Thalamic Radiations shown in FIG. 2A in the brain.
Figures 3A, 3B:
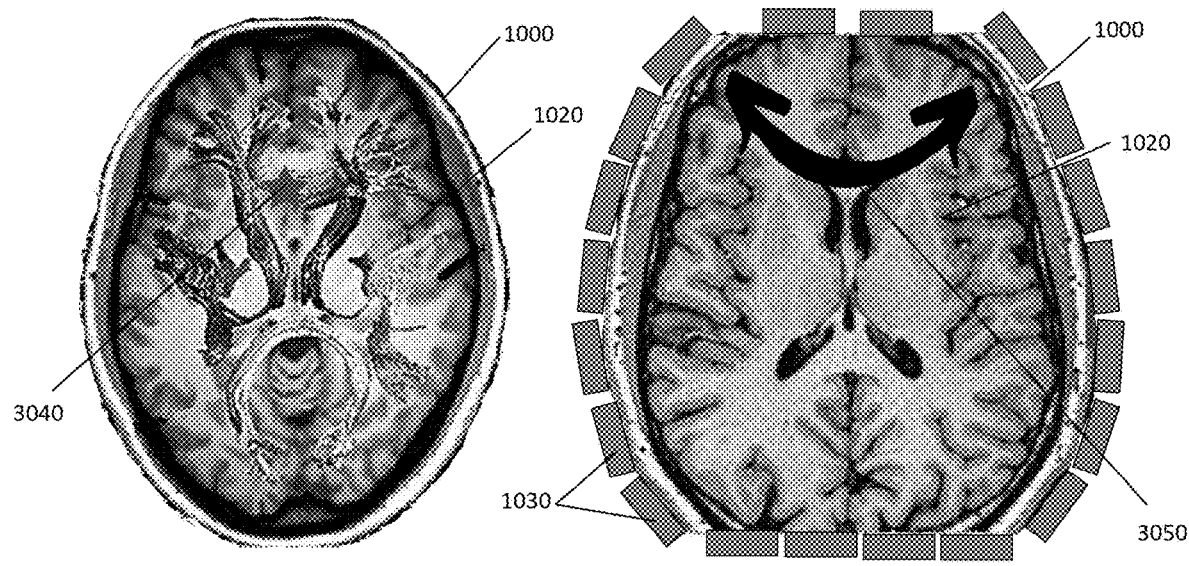
FIG. 3B is a 2-dimensional perspective view of a voltage gradient generated across the Forceps Minor shown in FIG. 3A in the brain.
Figure 4A:
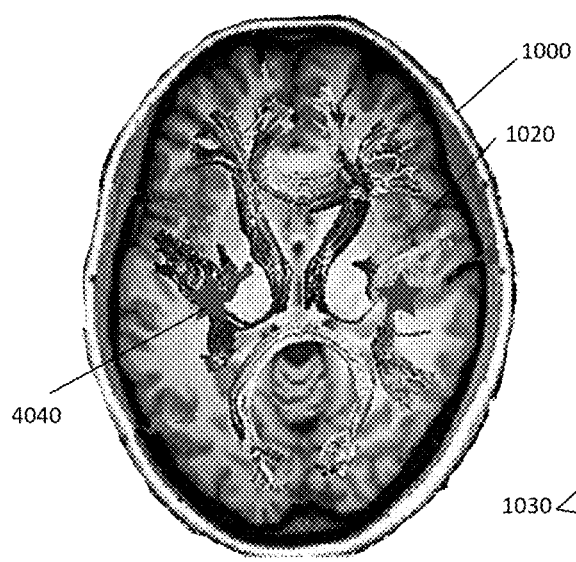
FIG. 4B is a 2-dimensional perspective view of a voltage gradient generated across the Superior Longitudinal Fasciculus shown in FIG. 4A in the brain.
Figure 4B:
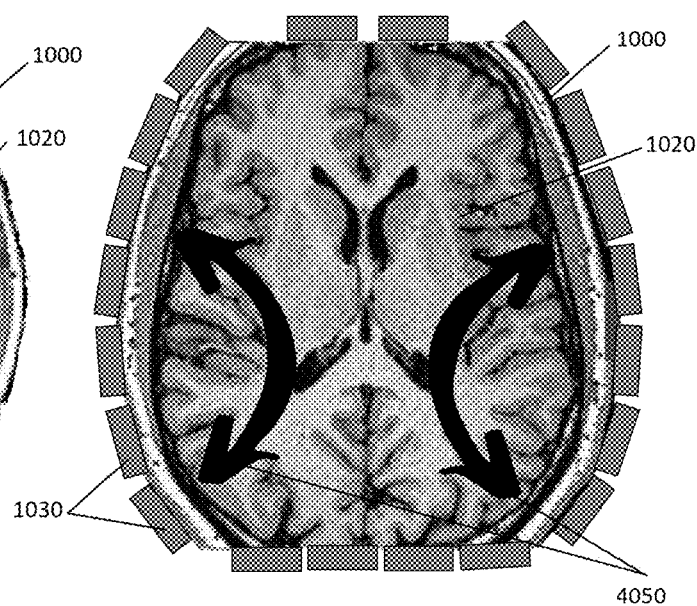
Figure 5A:
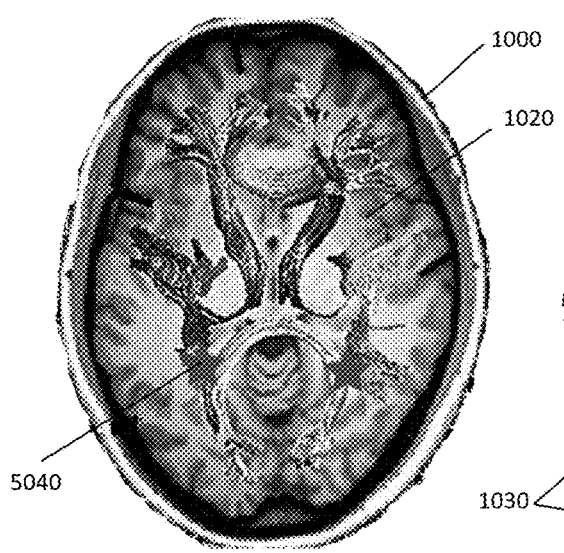
FIG. 5B is a 2-dimensional perspective view of a voltage gradient generated across the Interhemispheric Superior Longitudinal Fasciculus shown in FIG. 5A in the brain.
Figure 5B:
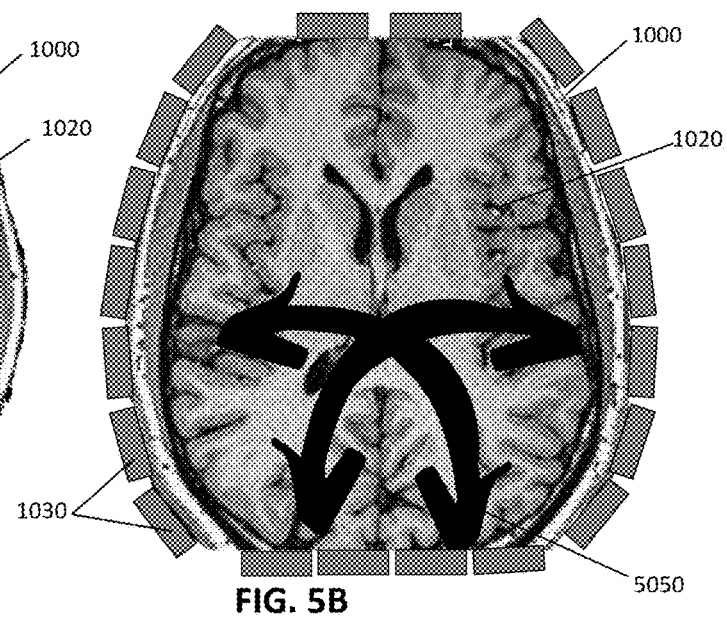
Figure 6A:
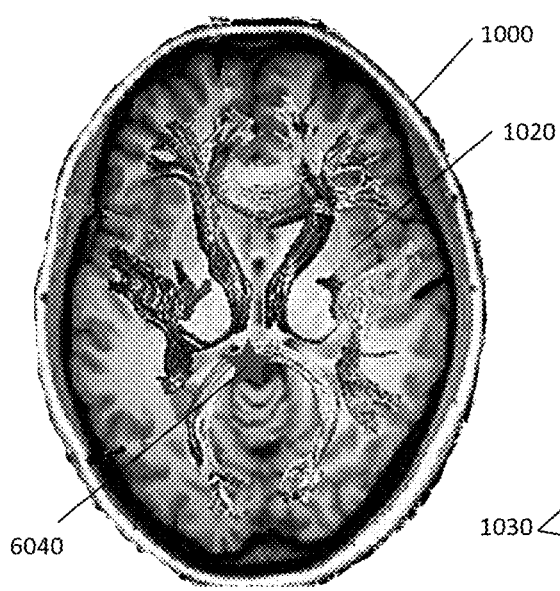
FIG. 6B is a 2-dimensional perspective view of a voltage gradient generated across the Forceps Major shown in FIG. 6A in the brain.
Figure 6B:
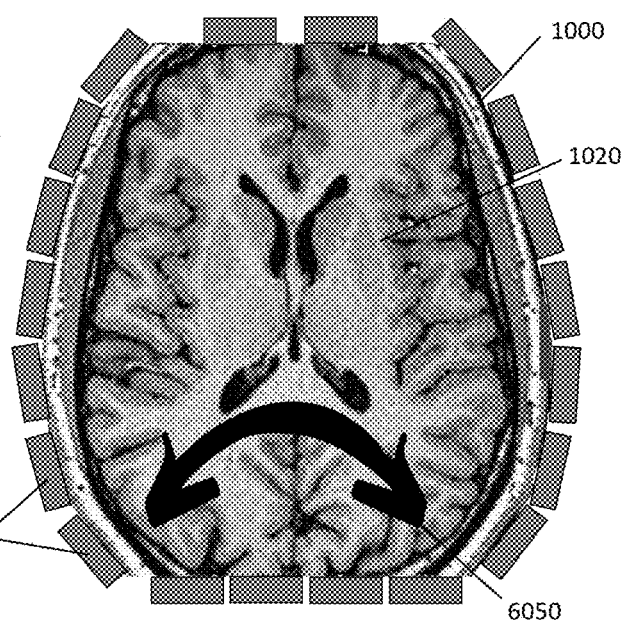
Figure 7:
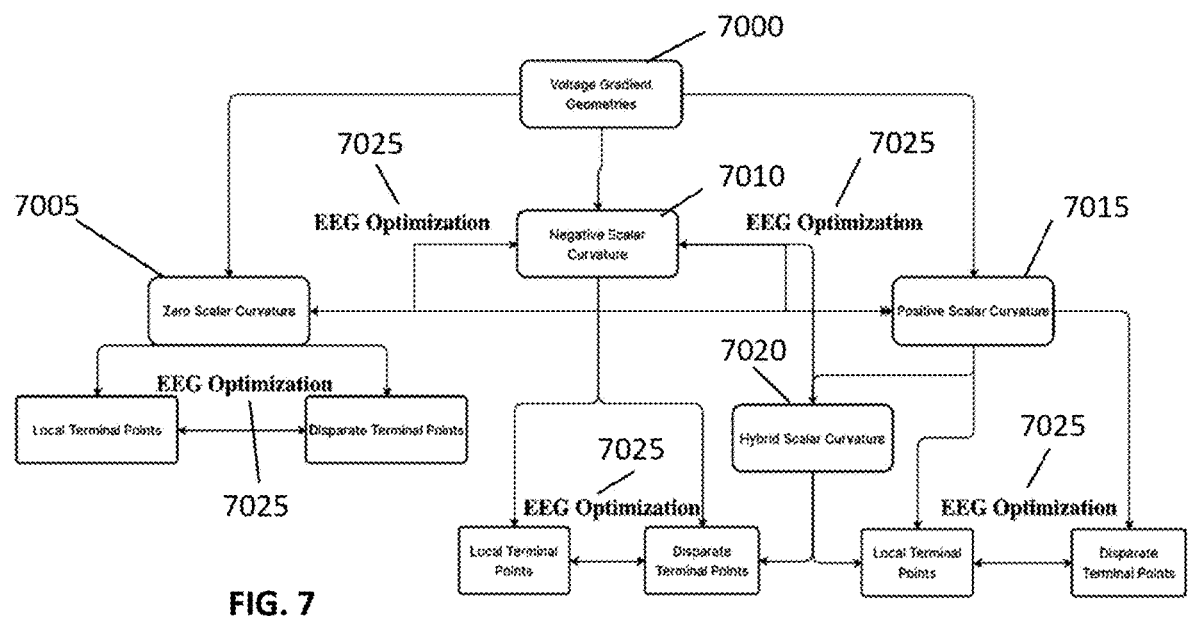
FIG. 7 is a flow chart of different voltage-gradient geometries classifications.
Figure 8:
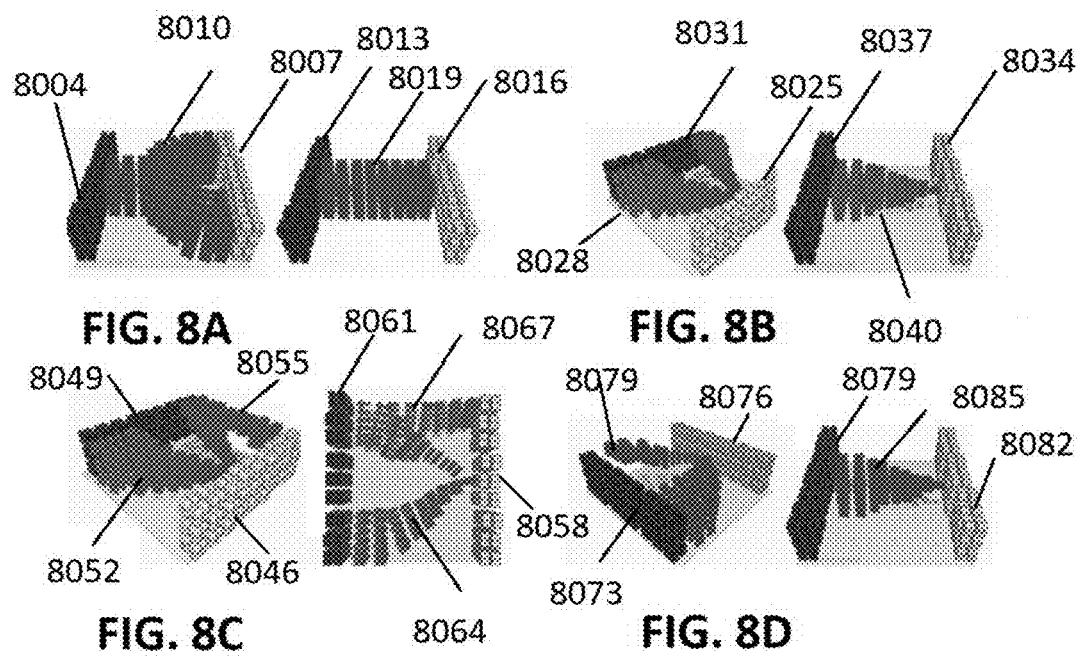
FIGS. 8A through 8D_are [is a] 3-Dimensional representations of different voltage-gradient geometries classifications with FIG. 8A demonstrating a Zero Scalar Curvature, FIG. 8B a Positive Scalar Curvature, FIG. 8C a Hybrid Scalar Curvature, and FIG. 8D a Negative Scalar Curvature.

FIG. 7 shows the flow chart and classifications of generating different geometric voltage gradients in 3-dimensional form as shown in FIGS. 8A through 8D, the Voltage Gradient Geometries Chart. In FIG. 7, the flow chart for generating Voltage Gradient Geometries 7000 has paths for generating Zero Scalar Curvature 7005, Negative Scalar Curvature 7010, Positive Scalar Curvature 7015, and via combining Negative Scalar Curvature 7010 and Positive Scalar Curvature 7015 getting the result of Hybrid Scalar Curvature 7020. In each case Local Terminal Points and Disparate Terminal Points (those where there are multiple targets on the anode electrode) with Direct Current or Pulsed Current being applicable to Local Terminal Points and Alternating Current and Random Noise applicable to Disparate Terminal Points. After EEG analysis, Post-EEG optimization 7025 of the voltage gradient curvature to and from positive 7015, negative 7010, and/or zero 7005 curvature is applied as well further optimization 7025 between the number of terminal points converting voltage gradient geometry to disparate and local gradient. here are three major scalar curvatures categories with voltage gradients (zero, positive, and negative) and 1 one sub-category (hybrid). Voltage gradients with more than two terminal points are called disparate voltage gradients while voltage gradients with only two terminal points are called local voltage gradients. Zero scalar curvature voltage gradients, FIG. 8A, are generated when the surface area of at least one terminal point on the cathode electrode 8004 that generates the voltage gradient is equal to the surface area of at least one terminal point on the anode electrode 8007 receiving the voltage gradient 8010 for the disparate case (where there is more than one target on the target anode). For the local case (where there is only one target on the target anode) of FIG. 8A, cathode 8013 is the source of voltage gradient 8019 with anode 8016 as the target. Positive scalar curvature voltage gradients shown in FIG. 8B are when the surface area of at least one terminal point on the cathode electrode 8025 for the disparate case and 8034 for the local case is less than the surface area of at least one terminal point on the anode electrode 8031 for the disparate case and 8037 for the local case receiving the voltage gradient 8028 for the disparate case and 8040 for the local case. Negative scalar curvature voltage gradients shown in FIG. 8D are when the surface area of at least one terminal point on the cathode electrode 8073 for the disparate case and 8079 for the local case is greater than the surface area of at least one terminal point on the anode electrode 8076 for the disparate case and 8079 in the local case receiving the voltage gradient 8079 for the disparate case and 8085 for the local case. Hybrid scalar curvature voltage gradients shown in FIG. 8C are when the surface area of many terminal points on the cathode electrode 8046 or 8058, both for the disparate case and 8058 for are both greater and less than the surface area of many terminal points on the anode electrode 8049 and 8061 receiving the voltage gradient, 8052 and 8055 or 8064 and 8067.

Figure 19:
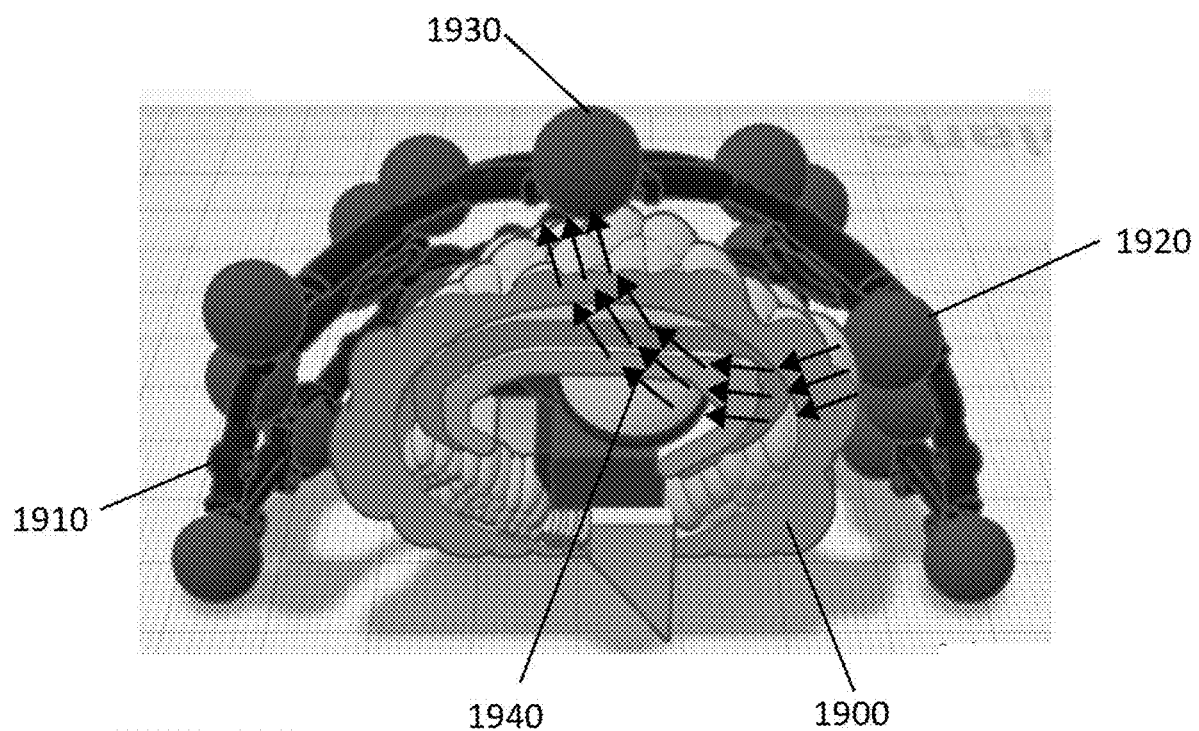
FIG. 19 is a 3-dimensional perspective view of a one Zero Scalar Curvature Local Voltage Gradient propagating in the brain from one cathode electrode on the visual cortex to the one anode electrode on the motor cortex.
Figure 20:
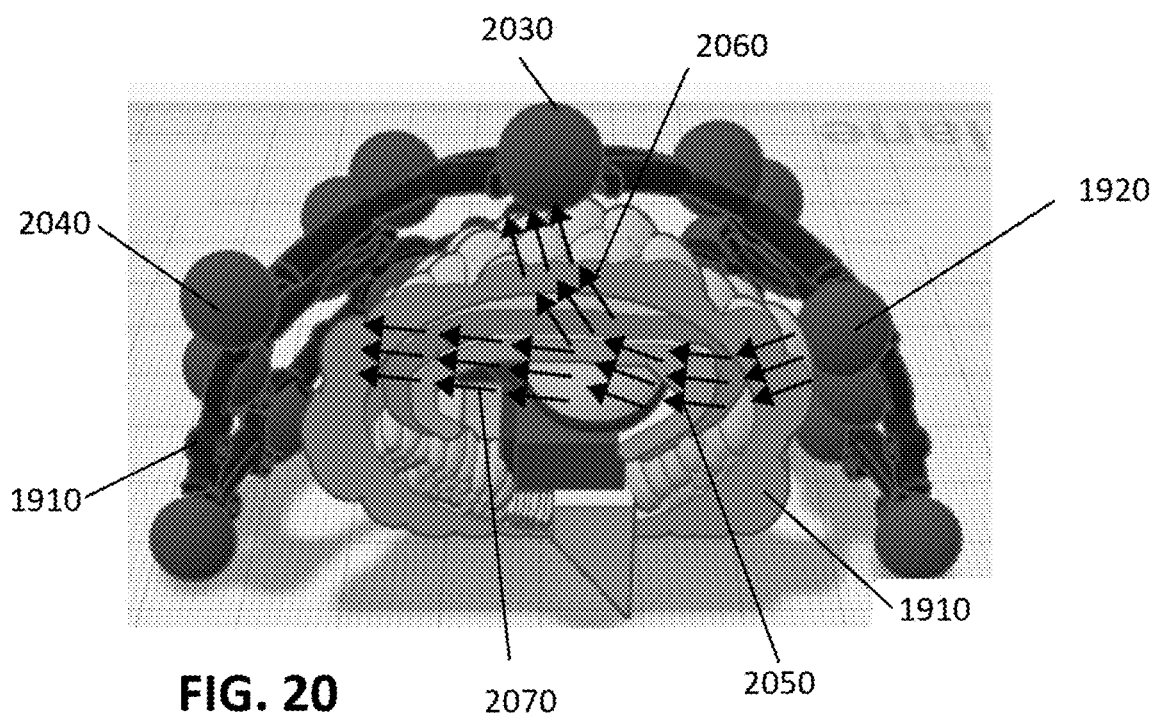
FIG. 20 is a 3-dimensional perspective view of a one Zero Scalar Curvature Disparate Voltage Gradient propagating in the brain from one cathode electrode on the visual cortex to one anode electrode on the motor cortex and one anode on the motor cortex.
Figure 21:
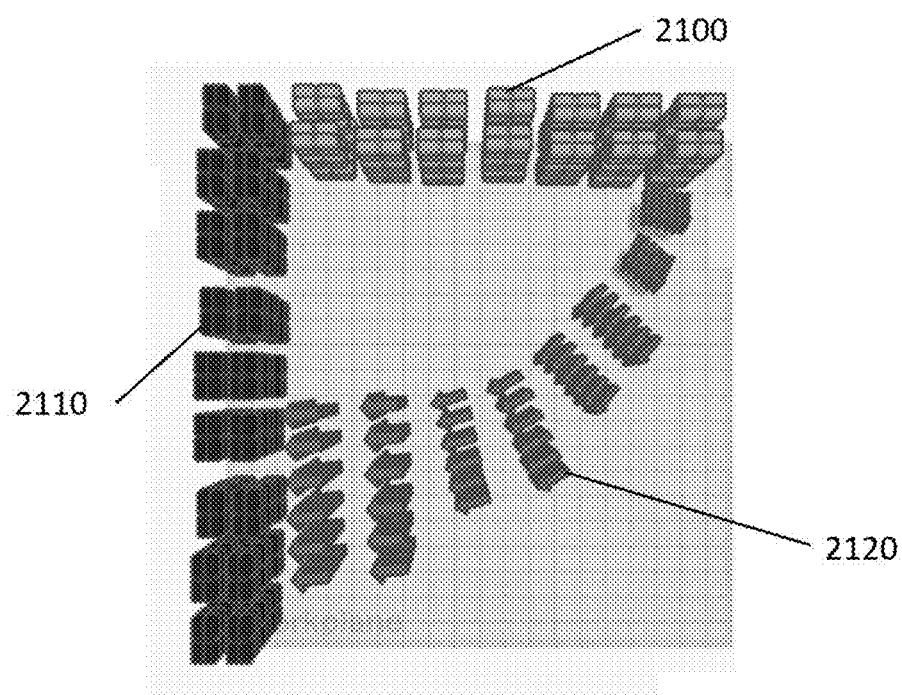
FIG. 21 is a 3-dimensional perspective top view of a one Positive Scalar Curvature Local Voltage Gradient propagating from two electrodes perpendicular with each other to highlight the importance of electrode positioning in modifying the geometry of the voltage gradient.
Figure 22:
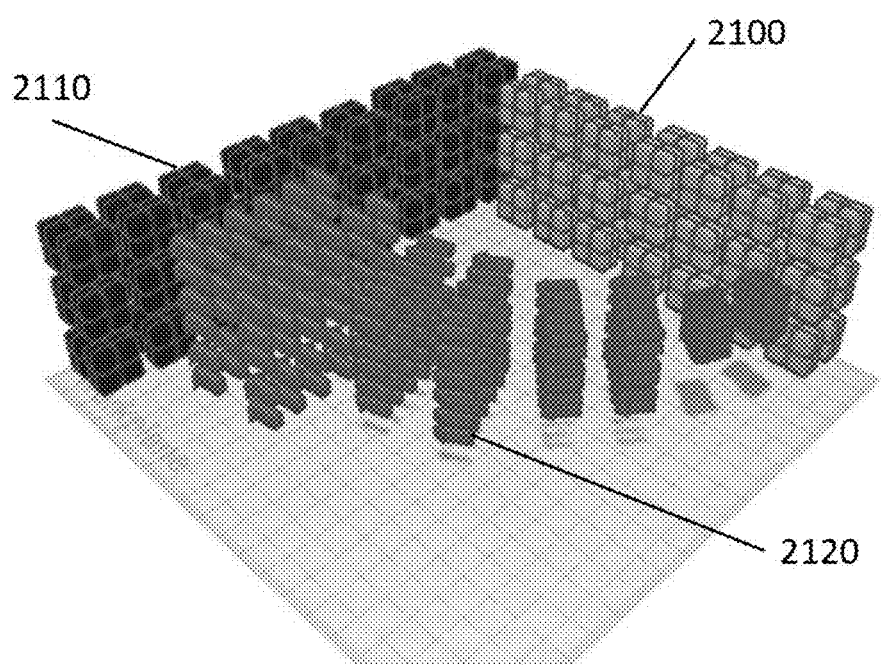
FIG. 22 is a 3-dimensional perspective angle view of a one Positive Scalar Curvature Local Voltage Gradient propagating from two electrodes perpendicular with each other to highlight the importance of electrode positioning in modifying the geometry of the voltage gradient.

There are 3 major ways to optimize the geometry of the voltage gradient which are 1) changing the dimensions of the cathode(s)/anode(s) with co-dependently of independently, 2) changing where in the array the cathode(s)/anode(s) are activated, and 3) changing how many terminal points or number of cathode(s)/anode(s) is being operated at a given point in time. By changing the dimensions of the cathode(s)/anode(s) we change the total volume of the voltage gradient, the curvature (Positive/negative/zero), and charge per area on different points of the gradient. A co-dependent change results in the size of the cathode(s)/anode(s) being changed simultaneously if the regression models instruct due to the total size of the tract being stimulated being larger/smaller than the voltage gradient geometry. The independent change is when the cathode(s)/anode(s) change individually depending upon the local geometry of the tract at the terminal points being larger/smaller than the predicted value. By changing the where in the array in which the cathode(s)/anode(s) is located, we change the total volume of the voltage gradient, the arc-length of the gradient, and we change the arc-angle of the voltage, gradient. The total volume of the voltage gradient will be affected to optimize the voltage gradient would deform across different curved tracts inside the brain. The arc-length is directly associated with the unit volume and allows for the voltage gradient to stretch longer/shorter across certain tracts of the brain while also modifying the total and unit charge per area of the voltage gradient along the tract. The importance of modifying the arc-length and subsequent total and unit charge per area is due to the needed potential to illicit actions potentials on neurons stretched along the tract. Different types of neurons with different threshold activation values, usually categorized through the 6 layers of the cortex, are arranged along the tract which then guides the understanding how the charge distribution along the tract should be arranged. The last variable of the voltage gradient geometry that can be modified is changing the number of terminal points that is being operated at a given point in time. FIGS. 19 and 20 display how the voltage gradient geometry would change in the brain based on the number of terminal points. In FIG. 19, the brain 1900 is covered by electrode holder 1910. The cathode 1920 sends out an electric field 1940 to meet the anode 1930 in one location. In FIG. 20, the brain is covered by electrode holder 1910. The cathode 1920 sends out a bifurcated electric field beginning with common section 2050 splitting into segment 2060 to meeting the first anode 2030 and segment 2070 meeting the second anode 2040. By changing the number of terminal points with the cathode(s)/anode(s) electrodes, there is a change in the total volume of the voltage gradient as well as the addition of separate arc paths in which the gradient lies upon. The rational for several distinct terminal points is the need to stimulate two or more tracts in the brain simultaneously. Furthermore, stimulating multiple distinct tracts simultaneously can allow for the coupling of endogenous oscillations of neuronal activity on the tract for positive clinical outcomes. FIGS. 21-22 further demonstrate the idea on modifying the voltage gradient geometry based on the positions of the electrode. By modifying the position of the electrode, the geometry of the voltage gradient changes significantly as it propagates from the cathode electrode contact to the anode electrode contact. In FIG. 21, in plan view, cathode 2100 is the source of voltage gradient 2020 that terminates in anode 2010. FIG. 22 shows the same configuration in a perspective view. Thus, this highlights the importance of electrode positioning to optimize the geometry of the voltage gradient around specific bundle tracts. Modifying the position of the electrodes changes the arc-length, arc-path, arc-angle, and charge per area of the gradient.

As shown in FIGS. 1B, 2B, 3B, 4B, 5B, 6B, 7, 8A, 8B, 8C, 8D, 9, and 10, voltage-gradient geometries can take on many different shapes. Optimizing the geometry of the voltage gradient through feedback mechanisms is important for increasing the purpose of sending the voltage gradient: whether it be inhibiting or enhancing a specific function. Many different feedback mechanisms exist both in vivo and in vitro. For in vivo, specifically in neurology, imagining techniques induce, but are not limited to: functional magnetic resonance imaging (fMRI), computerized tomography (CT), positron emission tomography (PET), electroencephalography (EEG), magnetoencephalography (MEG), functional near-infrared spectroscopy (fNIRS), electrical impedance tomography (EIT), Electrocorticography (ECoG), intracranial electroencephalography (iEEG), and magnetic impedance tomography (MIT). For the invention listed herein, we have used a closed-loop EEG-tCS feedback mechanism to modify the shape of the voltage gradient based upon different EEG markers. Markers are organized in 3 major categories: power spectral analysis, connectivity analysis, and microstate analysis. Parameters and markers in the power spectral analysis category are, but are not limited to: absolute power, relative power, alpha/beta to theta/delta ratio, dominant-frequency, peak-frequency, mean-frequency, frequency prevalence, ban inscription, compressed spectral array, neuronal activity topography, individual alpha frequency peak, and transition frequency. Parameters and markers in the connectivity analysis are, but are not limited to: coherence, phase lag index, phase-locking value, directed phase transfer entropy, lagged linear connectivity, global field synchronization, weighted network, and minimum spanning tree. Parameters and markers in the microstate analysis category are topographies, duration, occurrence, and coverage. Other types of mathematical models include, but are not limited to event-related potential, granger causality, graph theory measures, orthogonal decomposition, and proper orthogonal decomposition techniques. Using these techniques and others not listed, we can predict the shape of the voltage gradient produced through analysis of the EEG signal being acquired and then adjust the geometry of the voltage gradient to better fit the identified tract. FIGS. 11-14 show a pre-EEG optimized, zero scalar curvature, local voltage-gradients 1130, 1230, 1330, 1430, and a post-EEG optimized, zero scalar curvature, local voltage-gradients 1140, 1240, 1340, and 1440. Feedback to optimize the geometry of the voltage gradient in the brain is not limited to EEG and/or other neuroimaging techniques. Feedback variables can include heart-rate variability, electromyography (EMG), blood tests, nerve or skin biopsy, video monitoring of the body, and large imaging equipment such as CT or MRI scans. Other biomarkers include, but are not limited to: heart rate, heart rate variability, blood pressure, blood oxygen and/or carbon dioxide levels, body temperature, respiration rate, skin temperature, skin conductivity, and movement.

The vector field of the voltage gradient has a definitive shape that is defined through the 4 types of scalar curvatures mentioned above (positive, negative, zero, and hybrid). Through the identification of different imaging biomarkers to guide the understanding of neuronal tract orientations of the brain, the electrodes interactively modify the vector field change temporally through the cyclical interactions of voltage gradient deforming and imaging biomarker recording. The predicted deformation of the vector field is obtained through the computational of a path line integration of the mesh vertices derived from the predicted neuronal tract location. The deformation of the shape preserves the local and global electric field potential upon the voltage through the feedback tuning of the amount of current delivered based on the ratio of total current to the volume of voltage gradient as obtained through the path line integration. The approach of generating the voltage gradient shape based on predicted neuronal tract orientation can work at different iteration rates with a tradeoff between the accuracy of voltage gradient optimization and time to optimize. An independent user can perform the voltage gradient shape deformation, or the device can be automated to perform it independently. In both cases, the history of iterative voltage gradient shapes deformed is stored to allow the system to learn new optimization steps by analyzing the historical search space. When the user or device performs the first iteration of shape deformation, all edges of the deformed mesh representing the voltage gradient must be either longer or short than a certain threshold or between a certain range of angles of the normal of the mesh presenting the predicted neuronal tract. This threshold adaptation can allow users to optimize the voltage gradient shape with the intention of meeting certain clinical requirements of the electric field potential needed in a certain local and global area for pathological disruption such as High-Intensity electric field potential needed for Major Depressive Disorder or Low-Intensity electric field potentials needed for Amyotrophic Lateral Sclerosis.

The orientation of the voltage gradient depends upon the number of terminal points the voltage gradient has as well as the type of waveform the voltage gradient is being generated by. The introduction of more terminal points renders the algorithm to perform two separate shape deformations steps upon two sets of mesh vertices derived from one or more neuronal tracts in the brain. The two sets of mesh vertices of the voltage gradient may overlap as such, three separate shape deformation steps will be performed upon the collection of independent elements of the two sets of mesh vertices and one step on the overlapping elements. By defining the conduction direction of different electrical impulses, and action potentials, on a given tract, the force per unit charge of the electric field potential generated by the voltage gradient can be calculated with the charge variable being replaced by either 1) charge of single or collection of ions, 2) charge of single or collection of various neurotransmitter, 3) charge of single or collection of both ions and neurotransmitters, and 4) charge of any entity residing in the human brain that influences the action potential such as glial cells, peptides, hormones, and/or large internal neuronal structures. The conduction direction can take on two forms: antidromic and orthodromic. Antidromic refers to the conduction of an electrical impulse away from the axon terminal and towards the soma cell body. Orthodromic conduction is when the action potential starts at the cell body and funs along the axon of the neuron. Antidromic and Orthodromic conduction can be induced through electrical stimulation of a target structure and can be measured by local and global voltage changes on EEG time series. Thus, one can predict local line charge values along the tract temporally to optimize the direction and orientation of the necessary voltage gradient to induce a positive clinical response in the subject. The electric field strength is determined by the signal amplitude, current intensity, voltage levels, signal polarity, signal frequency, inter-signal width, and signal duration. The positive or negative flux of charge upon a neuronal tissue moves along the vector field path tangent to the mesh matrix of the voltage gradient.

Figure 11:
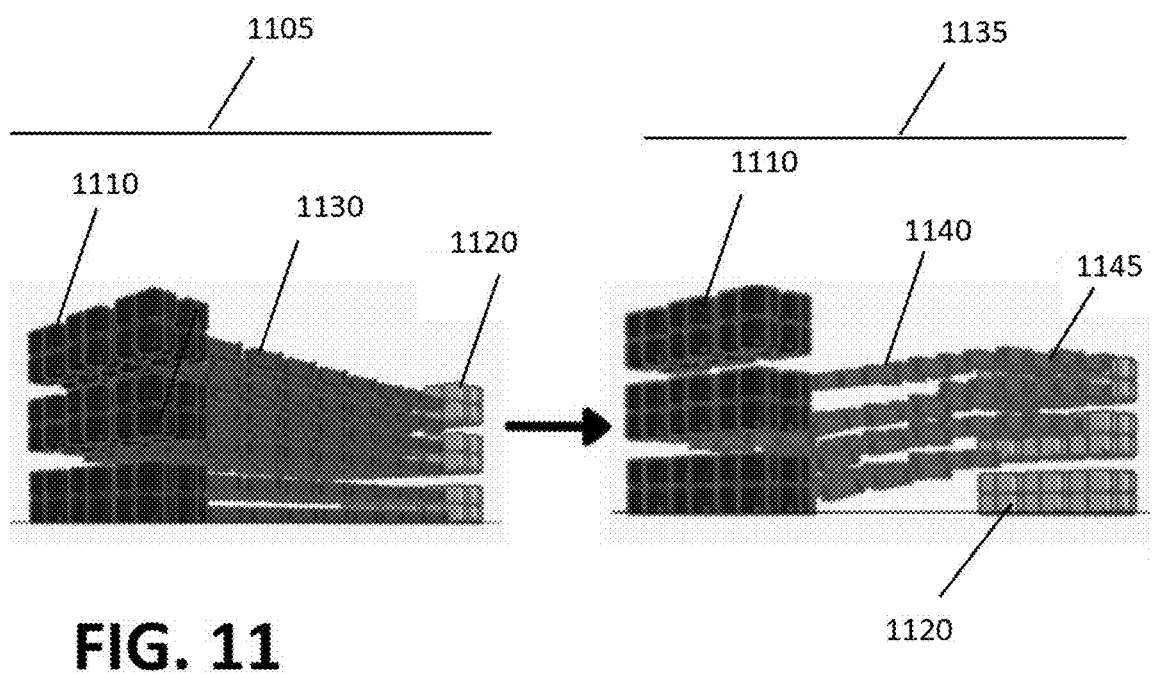
FIG. 11 is a 3-dimensional perspective view of a voltage gradient changing geometry after EEG optimization.
Figure 12:
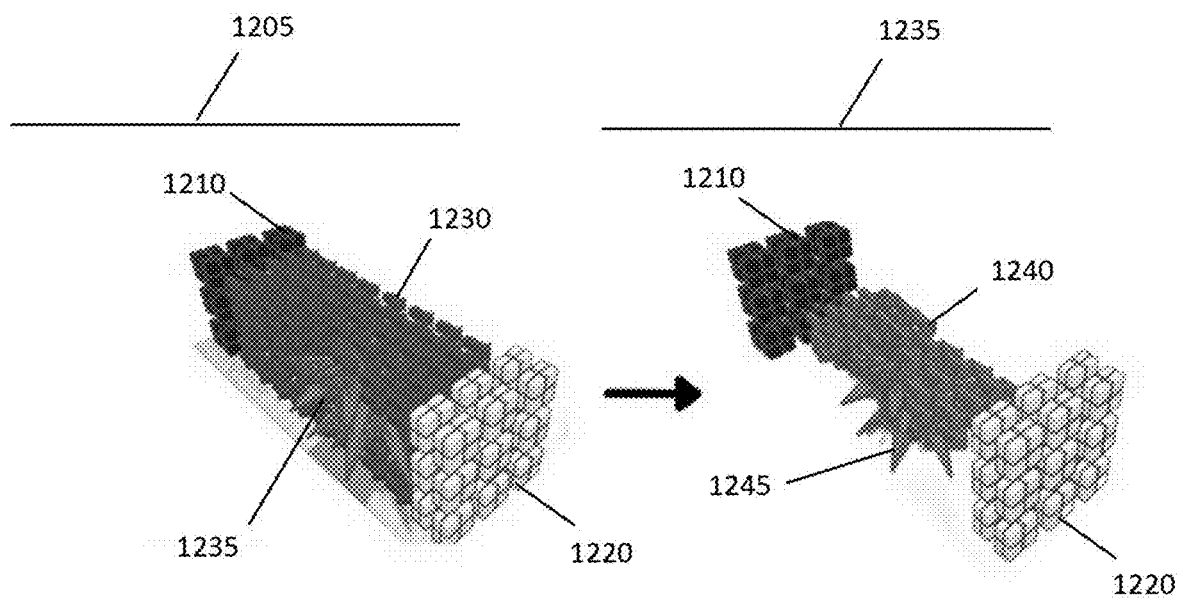
FIG. 12 is a 3-dimensional perspective view of a tract within a voltage gradient changing geometry after EEG optimization.
Figure 13:
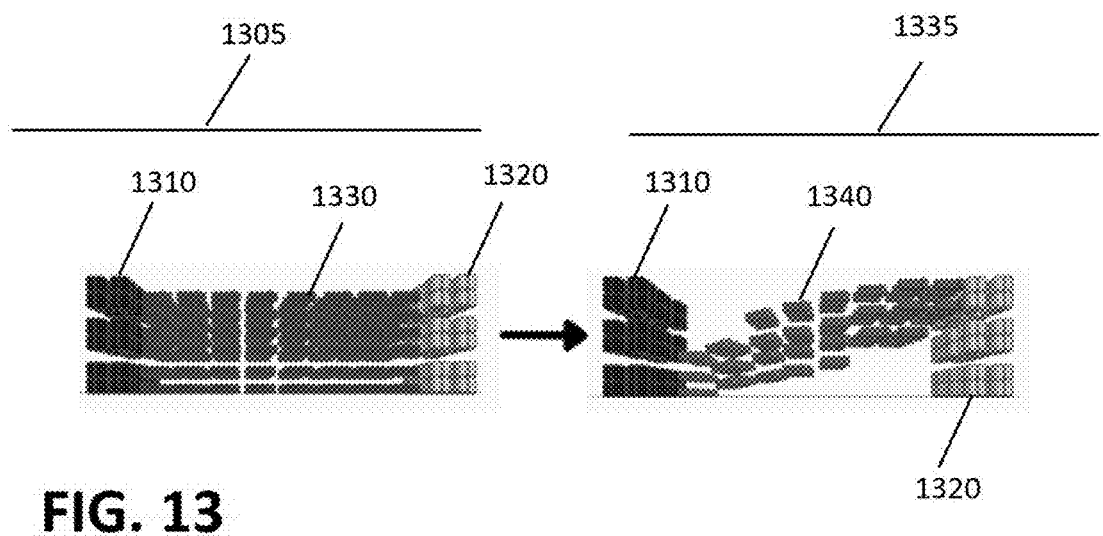
FIG. 13 is a 3-dimensional perspective view of a voltage gradient changing geometry after EEG optimization.
Figure 14:
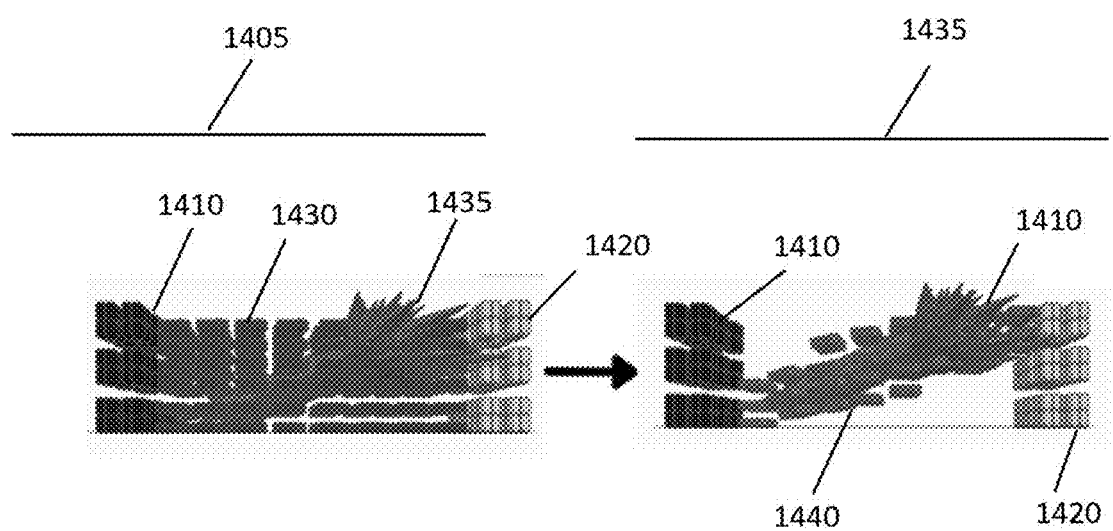
FIG. 14 is a 3-dimensional perspective view of a tract within a voltage gradient changing geometry after EEG optimization.
Figure 15:
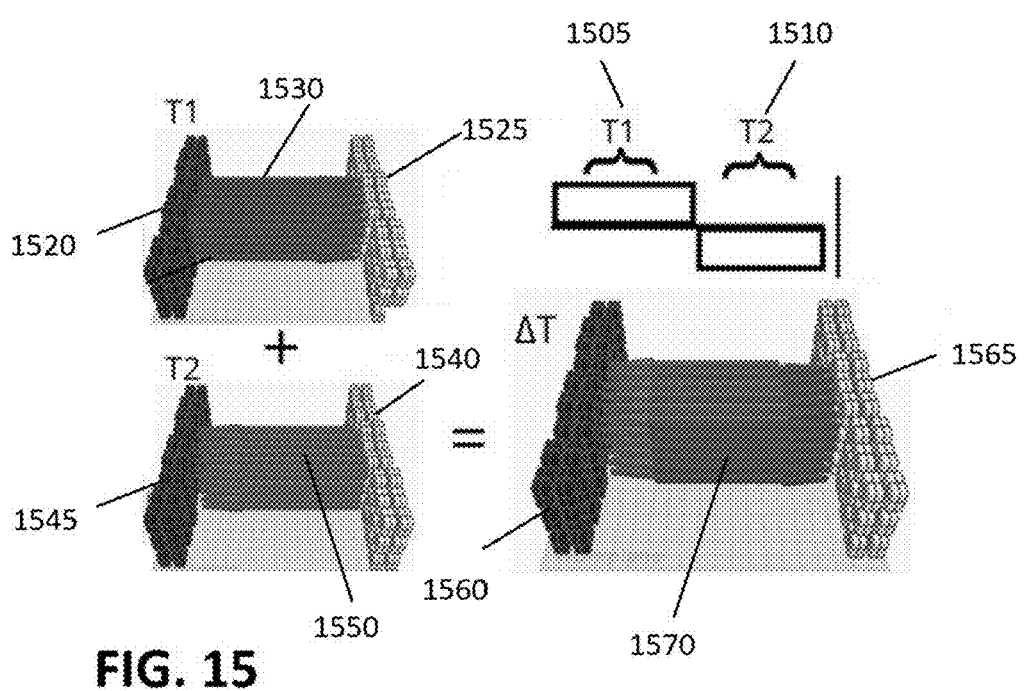
FIG. 15 is a 3-dimensional perspective view of a Zero Scalar Curvature Local Voltage Gradient created from a Direct Current/Amplitude Modulated Direct Current (DC/am-DC).
Figure 16:
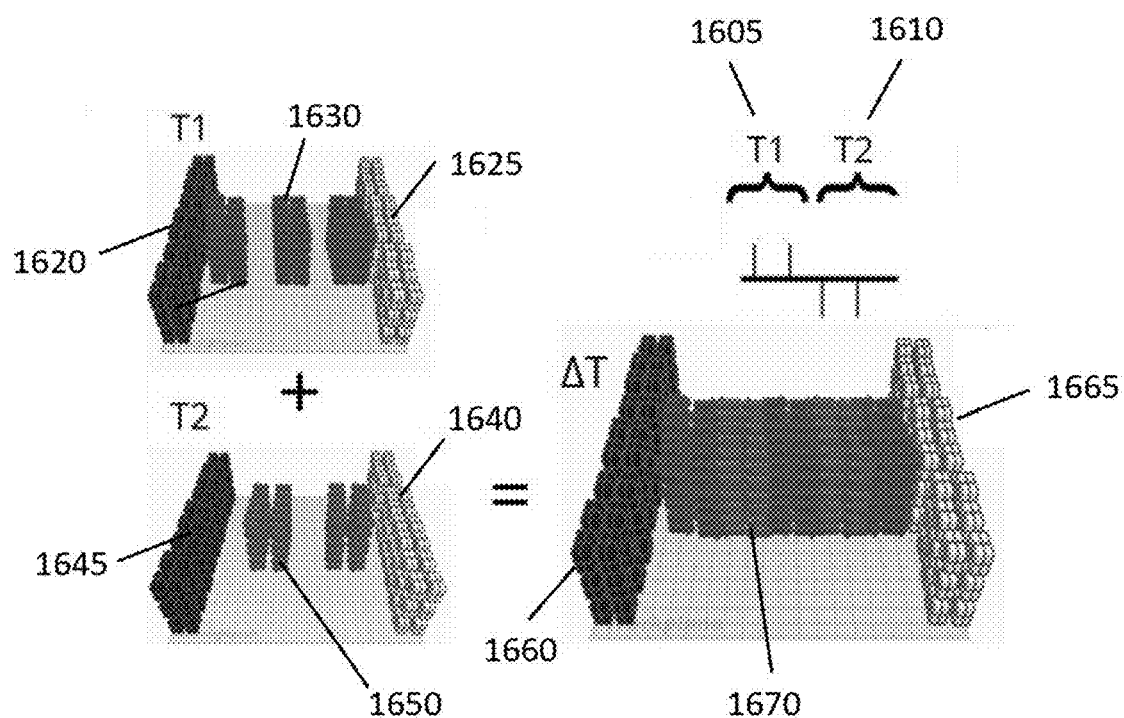
FIG. 16 is a 3-dimensional perspective view of a Zero Scalar Curvature Local Voltage Gradient created from a Pulsed Current/Amplitude Modulated Pulsed Current (PC/am-PC).

The position of the voltage gradient depends upon which neuronal tract is intended to be stimulated. There are three types of the tract in the brain: association fibers, commissural fibers, and projection fibers. Association tracts are tracts that connect cortical regions within the same hemisphere. Associated tracts are mainly inked to the perceptual and memory centers of the brain and are often impaired in different neurodegenerative disorders. The major association tracts in the brain and the regions they connect are 1) uncinate fasciculus connecting the frontal lobe and temporal lobe, 2) cingulum connecting the cingulate gyrus and entorhinal cortex, 3) superior longitudinal fasciculus connecting the frontal lobe and occipital lobe, 4) inferior longitudinal fasciculus connecting occipital lobe and temporal lobe, 5) vertical occipital fasciculus connecting inferior parietal lobule and fusiform gyrus, 6) occipitofrontal fasciculus connecting occipital lobe and frontal lobe, and 7) arcuate fasciculus connecting frontal lobe and temporal lobe. Projection fibers are tracts that connect the cerebral cortex to the spinal cord. Projection fibers consist of both efferent and afferent fibers in which efferent fibers carry signals away from a region to act on muscles and afferent fibers carry sensory signals towards a cortical region from the muscles. Furthermore, there are subcategories of projection fibers called commissural projective fibers that extend across the midline of the brain to connect the hemispheres; associative projection fibers that connect regions within a single hemisphere; and corticofugal projection fibers that extend away from the cortex. In neuromuscular disorders, diffusion tensor imaging from MRI scans showcases structurally abnormality in projection tracts and thus signal conduction between the brain and body for muscle control and sensation. The principal efferent projection fibers are 1) the motor tract consisting of the geniculate fibers and cerebrospinal fibers extending into the spinal cord and 2) the corticopontine fibers which terminate in the pontine nuclei. The principal afferent fibers are 1) lemniscus sensory fibers in the brain stem, 2) superior cerebellar peduncle, 3) optic fibers in the occipital lobe, and 4) acoustic fibers in the temporal lobes. The commissural fibers are fibers that connect the two cortical hemispheres together. The three commissural fibers are 1) the corpus callosum, 2) the anterior commissure and, 3) the posterior commissure. The corpus callosum is the largest commissural tract and plays an important role in problem-solving, verbal processing speed, and executive performance. It is shown that patients with neurodegenerative, neuropsychiatric, and neuromuscular disorders all have impaired structured and microstructural abnormalities of the corpus callosum related to cognitive dysfunction. Furthermore, extending out of the corpus callosum are two important commissural fibers which are the forceps major and minor. The anterior commissure connects the two temporal lobes of the hemispheres, is shaped like a bicycle as it branches through various areas of the brain and has been observed to have abnormalities in first-episode psychosis. The posterior commissure is a rounded nerve tract and lies on the dorsal aspect of the cerebral aqueduct. Researchers have shown that the posterior continues if important for pupillary light reflex and transferring information from the right occipital cortex to the language centers of the left hemispheres. In FIGS. 11-14, pre- and post-EEG optimized voltage gradients are shown with different perspective views, it is shown that the total volume of the voltage gradient post-EEG optimization is less indicating as well as the shape of the voltage gradient is deformed to better align with the neuronal tract shown more specifically in FIGS. 12 and 14. FIG. 11 illustrates Zero Curvature Voltage Gradient (Pre-EEG Optimization) 1105 showing the voltage gradient 1130 flowing between cathode 1110 and anode 1120. In Post-EEG Optimization 1135, the voltage gradient 1140 containing the impacted tract 1145 is modified flowing between cathode 1110 and anode 1120. FIG. 12 illustrates Tract within Voltage Gradient (Pre-EEG Optimization) 1205 showing the voltage gradient 1230 including tract 1235 flowing between cathode 1210 and anode 1220. In Post-EEG Optimization Tract with Voltage Gradient 1235, the voltage gradient 1240 containing the impacted tract 1245 is modified flowing between cathode 1210 and anode 1220 to increase the stimulation in the tract. FIG. 13 illustrates another example of Zero Curvature Voltage Gradient (Pre-EEG Optimization) 1305 showing the voltage gradient 1330 flowing between cathode 1310 and anode 1320. In Post-EEG Optimization 1335, the voltage gradient 1140 is modified flowing between cathode 1310 and anode 1320. FIG. 14 illustrates another Tract within Voltage Gradient (Pre-EEG Optimization) 1405 showing the voltage gradient 1430 including tract 1435 flowing between cathode 1410 and anode 1420. In Post-EEG Optimization Tract with Voltage Gradient 1435, the voltage gradient 1440 containing the impacted tract 1445 is modified flowing between cathode 1410 and anode 1420 to increase the stimulation in the tract. The 4 key hypotheses for optimization of the voltage gradient geometry's shape, orientation, and position are 1) increasing fractional anisotropy in a region of interest by eliciting action potential more precisely along the bundle tract, 2) optimizing ionic flow between two electrodes to move along the bundle tract, 3) inducing entrainment upon neuronal ensembles through the coupling of endogenous frequency by the precise activation of the bundle tract, and 4) better increase functional connectivity between 2 cortical regions, After recording the stream of signals from the EEG, or other types of biomarkers., the data goes through a pre-processing stage which includes the following: artifact subtraction, principal component analysis, blind source separation, and wavelet transform. Using the different types of signal analysis described above, one can modify the voltage-gradient geometry through the parameters described below. By having a 2-D dynamical electrode-contacts array that can modify the 3-D geometry of the voltage gradient, one can generate several different voltage-gradient geometries for a variety of purposes in biological media. Furthermore, one can modify the 3-D geometry of the voltage gradient through the shape of the pulse/signal/waveform (the word waveforms will be used from henceforth) being delivered. There are two major categories of waveform modulation: analog and digital. Ways to modulate these waveforms include, but are not limited to Pulse-amplitude modulation (PAM) Pulse-width modulation (PWM), Pulse-frequency modulation, and/or (PFM) Pulse-position modulation (PPM). This is done by modulating the current through a driver circuit under microcontroller control. FIGS. 15-18 show examples of how the geometry of the voltage gradient changes according to the waveform being delivered. FIG. 15 demonstrates Direct Current/Amplitude Modulated Direct Current (DC/am-DC) with Zero Scalar Curvature Local Voltage Gradient. In FIG. 15, the T1 component of the voltage-gradient 1505 of the amplitude modulated direct current waveform is applied with voltage gradient 1530 flowing between cathode 1520 and anode 1525. The T2 component of the voltage gradient 1510 of the amplitude modulated direct current waveform is applied with voltage gradient 1550 flowing between cathode 1540 and anode 1545. The combined result AT has electrodes 1560 and 1565 each alternating roles between cathode and anode and produces the consequent directionally alternating voltage gradient 1570. The voltage-gradient geometry in FIG. 15 is a local, zero scalar curvature voltage gradient. FIG. 16 demonstrates the Pulsed Current/Amplitude Modulated Pulsed Current (PC/am-PC) with Zero Scalar Curvature Local Voltage Gradient. In FIG. 16, the T1 component of the voltage-gradient 1605 of the amplitude modulated pulsed current waveform is applied with voltage gradient 1630 flowing between cathode 1620 and anode 1625. The T2 component of the voltage gradient 1610 of the amplitude modulated pulsed current waveform is applied with voltage gradient 1650 flowing between cathode 1640 and anode 1645. The combined result AT has electrodes 1660 and 1665 each alternating roles between cathode and anode and produces the consequent directionally alternating voltage gradient 1670. The voltage-gradient geometry in FIG. 16 is a local, zero scalar curvature voltage gradient.

The prediction of functionally connected networks derived from EEG signatures can be determined through statistical associations between EEG activity and underlying sub-cortical to cortical structural brain connectivity determined by probabilistic white matter tractography. This is done by evaluating dynamic cortical brain activity and inferred functional networks to underlying white matter connectivity in distinct frequency bands. It was found that the white matter cortical network derived from EEG partially reflects both direct and indirect underlying white matter connectivity. The Co-registrations of EEG and fMRI DTI data allow researchers to find signatures of different EEG and correlate them to structural tractography information in the brain. White matter connectivity and the terminal points on the surface of the cortex of different neuronal tracts is associated with the functional connectivity of high voltage spikes on EEG data. Thus, through high-resolution and ultra-dense EEG sensors, predictive analytics with the assistance of machine learning can be used. Machine learning is the identification of the different relationships between several variables using regression models. One of the key dependent variables in which the voltage gradient geometry will be optimized is various clinical outcomes for different neurological disorders. Clinical outcomes are the measurable change in symptoms, overall health, ability to function, quality of life, or survival outcomes that result from giving care to patients. The variables that can be compared between the EEG, clinical endpoints, and other biomarker modalities can be correlated with 3 types of regression models to optimize the voltage gradient geometry are, 1) a simple regression model, 2) a multiple regression model, and 3) Multiple target regression. To expand upon further, simple regression models aim to fit a linear regression model between one independent variable and one dependent variable. Multiple regression models aim to find a statistical fit between two or more independent variables and one dependent variable. Multiple target regression models aim to find a statistical fit between two or more independent variables and two or more dependent variables.

Simple Linear regression models apply when finding the relationship between two variables such as EEG alpha power and percentage of tremor reduction. The two variables act as a predictor and responses, where one variable predicts the response of the other. This is a purely statistical relationship and not necessarily a deterministic causal relationship between the two variables. The essence of simple linear regression models is to obtain a line that best fits all the data and in which the total prediction error (distance between the regression line and point) is minimized. The Pearson correlation provides an indicator of the strength of association between 2 variables where a value of 1 means that the two variables are perfectly correlated, 0 means that are not correlated, and −1 where the two variables are negatively correlated. For simple linear regression models, there are 4 key principles that are assumed in the dataset being analyzed: 1) linearity and additivity, 2) statistical independence, 3) homoscedasticity, and 4) normality. Linearity and additivity between the dependent and independent variables indicate that a straight-line function of each independent variable is expected that this slope does depend upon the values of other variables, and that the effects of different independent variables are additive. Statistical independence means that every error generated by a data point is independent of any error generated by another data point. Homoscedasticity refers to the value of the error term does not vary as much as the variance of the independent variable. Normality refers to the total difference between the observed value and the estimated values following a normal distribution.

Multiple regression models with multiple variables make up the main disadvantage of simple linear regression which is running separate regression for multiple datasets. There are several types of multiple regression models: ordinary least squares method, gradient descent, and regularization. Ordinary least squares methods (OLS) choose the unknown parameters in a linear regression through the process of minimizing the sum of the squares of the differences between the observed variables and the output function of the independent variable. In other words, it is the sum of the squared distances between each data point and the regression line or surface. Gradient descent is when the regression model of one or more inputs is optimized by iteratively minimizing the error of the model. In other words, it attempts to find a local minimum of a differential function through iterative steps against the direction of the steepest descent of the function at a given point. Regularization methods seek to minimize the sum of the squared error of the model on the training data while also reducing the complexity of the model. The two most common regularization methods are 1) lasso regression and 2) ride regression. Lasso regression is like the ordinary least squares method while also minimizing the absolute sum of the coefficients to shrink the data with L1 regularization. Ride regression is similar to lasso regression with the replacement of L1 regularization with L2 regularization. Multiple target regression (MTR) is where multiple independent variables aim to find a fit with various dependent variables. MTR is built on predictive clustering trees which use decision trees to shrink the complexity of the data. Each leaf of the tree corresponds to a concept or a cluster and the nodes of the tree indicate a hierarchy that labels different categories with the order. In supervised classification, the measure of the distance between two variables indicates the way in which the two variables are related or clustered. Moving down the decision tree is like going from a large cluster to a smaller cluster at the bottom. To build a decision tree, the distance measure and the prototype function must be selected. The distance measures the manner in which 2 instances can be measured such as Euclidean Distance, Cosine Similarity, Hamming Distance, Manhattan Distance, Chebyshev Distance, Minkowski, Jaccard Index, haversine and Sorenson dice measures. A prototype function is the predefined center of a cluster such that 2 clusters can be computed. Predictive clustering trees identify the specific test that minimizes the distances between clusters. MIR is more advantageous than other methods because it optimizes for all targets together rather than just a single target as well as MTR trees provide models that are easily interpreted by humans.

Furthermore, there are three other main methodologies of voltage gradient geometry optimization: empirical, theoretical, and hybrid. Empirical methods rely on direct and/or indirect observation of physiological processes and/or variables to voltage gradient geometries based on real-time evidence. Theoretical methods create abstract models of physiological process and/or the independent variables to guide voltage gradient geometry which are then tested for validity. Hybrid methods use direct and/or indirect observation of physiological processes and/or the variables to tune abstract models of these processes and/or the variables to guide the voltage gradient geometry based using both empirical and theoretically driven methods. All three methods will be detailed below on how to optimize geometry of the voltage gradient.

Empirical driven methods look at real-time variables, such as the different components and analysis techniques of the EEG, and adjusts the voltage gradient geometry according to the most optimal state of the EEG. The most common empirical method for voltage gradient geometry optimization is through parametric and/or nonparametric Bayesian optimization. There are two stages to Bayesian Optimization that repeat iteratively: the data-modeling stage and guided-search stage. In the data modeling stage, the objective function, a function that is desired to be maximized or minimized, is estimated through a probabilistic surrogate model with a model known as a posterior, which is an artificial model created due to limitations of collecting data from the real model. Furthermore, Bayesian optimization usually requires scalar responses. A functional linear model with scalar responses is a regression model where the predictor is a functional random variable, and the response is a real random variable defined on the same probability space. After the data-modeling stage comes the guided-search stage where an acquisition function is used to propose two points in the parameter space from which to sample next. For example, choosing two blocks with different voltage gradient geometries that the subject will be stimulated with next. The acquisition function thus balances the trade-off between parameter space exploration and parameter leveraging for which measurements have been collected which ultimately allows for an efficient and reliable search over an exhaustive parameter space.

Theoretically driven methods drive voltage gradient geometry optimization through abstract models of physiological processes with 2 or more variables which then guide parameter-space exploration during closed-loop sensing-stimulating applications. For example, it is well known that large voltage gradients volumes, the total area the voltage gradient occupies in the brain, can lead to extreme phosphenes and adverse skin reactions while smaller voltage gradients volumes lead to zero adverse effects. Thus, a linear relationship between two variables, volume of voltage gradient and adverse reactions, can be modeled which then acts as an objective function to be minimized. Voltage gradients volumes also has a linear dependence with another variable, spike activation of neurons. This produces an objective function which is desired to be maximized. As such, voltage gradients volumes, adverse effects, and spike activation produce a 3-dimensional model of which some variables need to be maximized while other variables need to be minimized. After development of objective functions through theoretical abstraction, the Bayesian guided search stage can be initiated to find points on the parameter space of which voltage gradient volume to sample next, as discussed in the empirical methods above. For direct comparison, empirical methods use probabilistic surrogate models to estimate objective function(s) based upon newly observed data while theoretical methods use predetermined multivariable models to act as the objective function(s) to guide voltage gradient geometry optimization. Empirical methods use models derived from observed data from the experiment. Theoretical methods use predetermined models from previously observed data of other experiments abstracted through reasoning.

Hybrid driven methods utilize the theoretical predetermined models and adapt specific variable relationships based upon observed data. For example, if a well-known predetermined model between voltage gradients volumes and adverse events is used as the objective function while an outlier subject shows zero adverse events at voltage gradients volumes, then the predetermined model is then adjusted for the subject. Thus, the guided search stage will then find a point of the parameter space outside the predetermined maximum/minimum of the previous objective function until a new maximum/minimum is found for the specific patient. Hybrid driven methods are the most robust, adaptable, and personal approach to optimize voltage gradients geometries based upon both predetermined models and newly observed data. However, due to the ability to adjust the objective function(s) based upon new data, hybrid approaches have longer time-costs. Due to infinite parameter space that can be sampled for optimizing the geometry of the voltage gradient, active sampling approaches have been developed to choose samples in real-time. Active sampling is used when exploring large parameters spaces of conditions and when the data needed to efficiently explore the space comes at a cost (financial, energy, time). Parametric Bayesian methods are traditionally used where the statistics of the parameter search are based on assumptions about the data from which the sample was taken. However, these assumptions are difficult to justify given the limited prior knowledge on the data of the physiological processes and/or biomarkers at hand. Nonparametric Bayesian optimization of voltage gradient geometry is not based on assumptions and understands that the data being collected from the biomarkers does not follow a specific distribution. They are also a lot faster than parametric approaches and offer a lot more flexibility to accommodate many different types of functions.

Waveform and voltage-gradient geometry modulation can be further personalized to the patient and/or subject wearing the invention. The waveform and voltage-gradient geometry modulation are then personalized to specific EEG signatures throughout a single session, day, week, month, year, or any other range of time. Waveforms and voltage-gradient geometry personalization over time (in-session, days, weeks, months, and years) allow for the brain to reach higher states of plasticity through electric stimulation which can be used for both wellness and therapeutic applications for the treatment of neurodegenerative, neuromuscular, and neuropsychiatric disorders such as, but not limited to, Alzheimer's Disease and other Dementia disorders, Ataxia, Huntington's Disease, Parkinson's Disease, Motor Neuron Disease, Multiple System Atrophy, Multiple Sclerosis, and Progressive Supranuclear Palsy. As an example, the device will change the amount of total charge that is being delivered into the brain over time such that the total charge in the first week is 50% of the total charge in the second week, and 25% in the third week. The numbers, percentage, and ratios of the relative and absolute total charge from week to week can be modified per subject, geography they are located in, time of year they use the device, age of the subject, and other environmental variables including, but not limited to: weather, season, climate, culture, economic status, and altitude. The application of the stimulation is not strictly limited to the generation of voltage gradients via electrical stimulation and current drivers. Red/blue/green/infra-red light therapies, transcranial magnetic stimulation (TMS), transcranial direct current stimulation (tDCS), transcranial random noise stimulation (tRNS), transcranial pulsed current stimulation (tPCS), transcranial alternating current stimulation (tACS), transcranial alternating pulsed current stimulation (tAPCS), transcutaneous electrical nerve stimulator (TENS), invasive vagus nerve stimulation (i-VNS), noninvasive vagus nerve stimulation (ni-VNS), spinal cord stimulation (SCS), and pulsed electromagnetic field therapy (PEMF) can all be used to generate voltage-gradient geometries and modifying the shape of the gradients through different feedback modalities. Furthermore, one can send many different types of voltage-gradient geometries (analog, pulsed, digital, random), in a singular session to optimize the effects of the voltage-gradient geometries on a given function, activity, or cellular process during different times of the day. Activities can include sleeping, meditation, athletic performance, playing an instrument, solving a puzzle, learning a language, studying a subject, operating heavy machinery or motor vehicle, praying, and/or singing; all activities can be recorded and optimized by generating voltage-gradient geometries specific regions of interests in biological tissue to enhance a function or cellular process. Lastly, generative specific shaped voltage-gradient geometries with feedback mechanisms are not limited to just humans, the inventions and methods described herein can be extended to other in vivo applications such as mammals, mammalian cadavers, and other organisms as well in silico applications with software computational modeling, and in vitro biological tissues including, but not limited to, cells derived from multicellular organisms, subcellular component, cell or tissue cultures, cellular or subcellular extracts, purified molecules, and pharmaceutical products.

Figure 17:
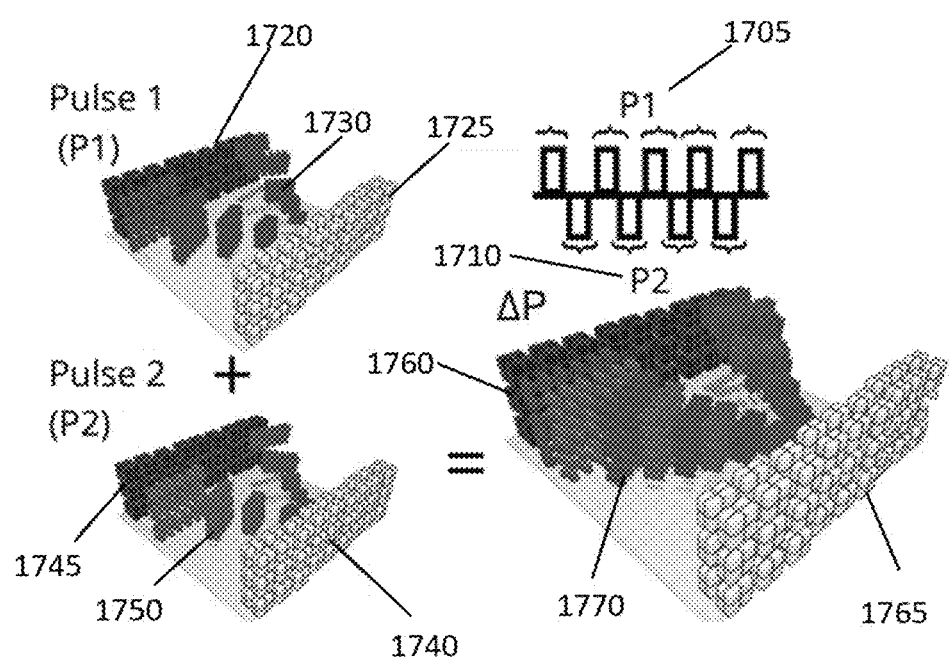
FIG. 17 is a 3-dimensional perspective view of a Negative/Positive Scalar Curvature Disparate Voltage Gradient created from an Alternating Pulsed Current/Biphasic Current (APC/BC).
Figure 18:
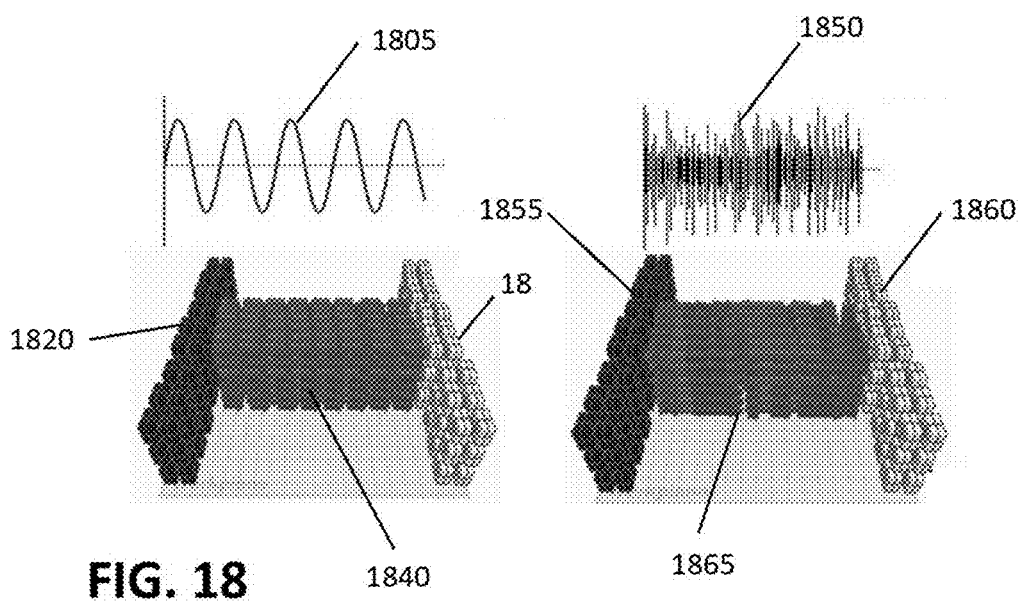
FIG. 18 is a 3-dimensional perspective view of two Zero Scalar Curvature Local Voltage Gradients created from an Alternating Current/Sinusoidal Current (AC/SC) and a Random-Noise Current/Chaotic Current (RNC/CC).

FIG. 17 demonstrates the Alternating Pulsed Current/Biphasic Current (APC/BC) with Negative/Positive Scalar Curvature Disparate Voltage Gradient. In FIG. 17, the P1 component of the voltage-gradient 1705 of the alternating pulsed current/biphasic current waveform is applied with voltage gradient 1330 flowing between cathode 1720 and anode 1725. The T2 component of the voltage gradient 1710 of the alternating pulsed current/biphasic current waveform is applied with voltage gradient 1750 flowing between cathode 1740 and anode 1745. The combined result ΔT has electrodes 1760 and 1765 each alternating roles between cathode and anode and produces the consequent directionally alternating voltage gradient 1770. In FIG. 17, the positive polarity pulses denoted P1 1705, create a voltage gradient with a negative scalar curvature, and the negative polarity pulses, denoted P2 1710, create a voltage gradient with a positive scalar curvature. The overall voltage-gradient geometry from the biphasic pulsed current, also known as alternating pulsed current, creates a disparate, negative/positive scalar curvature voltage gradient that switches between positive and negative curvature depending upon the polarity of the isolated pulse in the waveforms. Lastly, FIG. 18 shows the voltage-gradient-geometry generated by voltage gradient 1840 flowing between electrodes 1820 and 1830 where electrodes 1820 and 1830 each alternate roles between cathode and anode from an alternating/sinusoidal current waveform 1805 and the voltage-gradient-geometry generated by voltage gradient 1865 flowing between electrodes 1855 and 1860 where electrodes 1855 and 1860 each alternate rol[d]es between cathode and anode from a random-noise/chaotic current waveform 1850. It should be noted that there is a large waveform parameter space used to generate different voltage-gradient geometries that are not pictures; parameters include, but are not limited to signal amplitude, current intensity, voltage levels, signal polarity, signal frequency, inter-signal width, and signal duration. Thus, not all voltage-gradient geometries have been pictured, however, the method to generate, optimize, and categorize different voltage-gradient geometries through feedback mechanisms is listed. The generation of dynamic voltage-gradient geometries in the mammalian brain is not limited to transcranial stimulation; the application of voltage gradient and modification of voltage-gradient geometries can be done through minimally invasive and invasive electrical stimulation methods including, but not limited to: stereo electroencephalography, Electrocorticography/intracranial electroencephalography, and deep brain stimulation. Furthermore, the generation of dynamic voltage-gradient geometries can occur both in vivo (mice, rats, rabbits, non-human primates) and in vitro (stem cells, Petri dishes, model cells). The subcellular, cellular, and network effects in mammals from the generation of voltage gradients include, but are not limited to: increased angiogenesis, increases blood flow, anti-inflammation, increased synaptogenesis, anti-apoptosis, reduced neuronal excitotoxicity, increased neurotrophins, and increased antioxidants.

Figure 23:
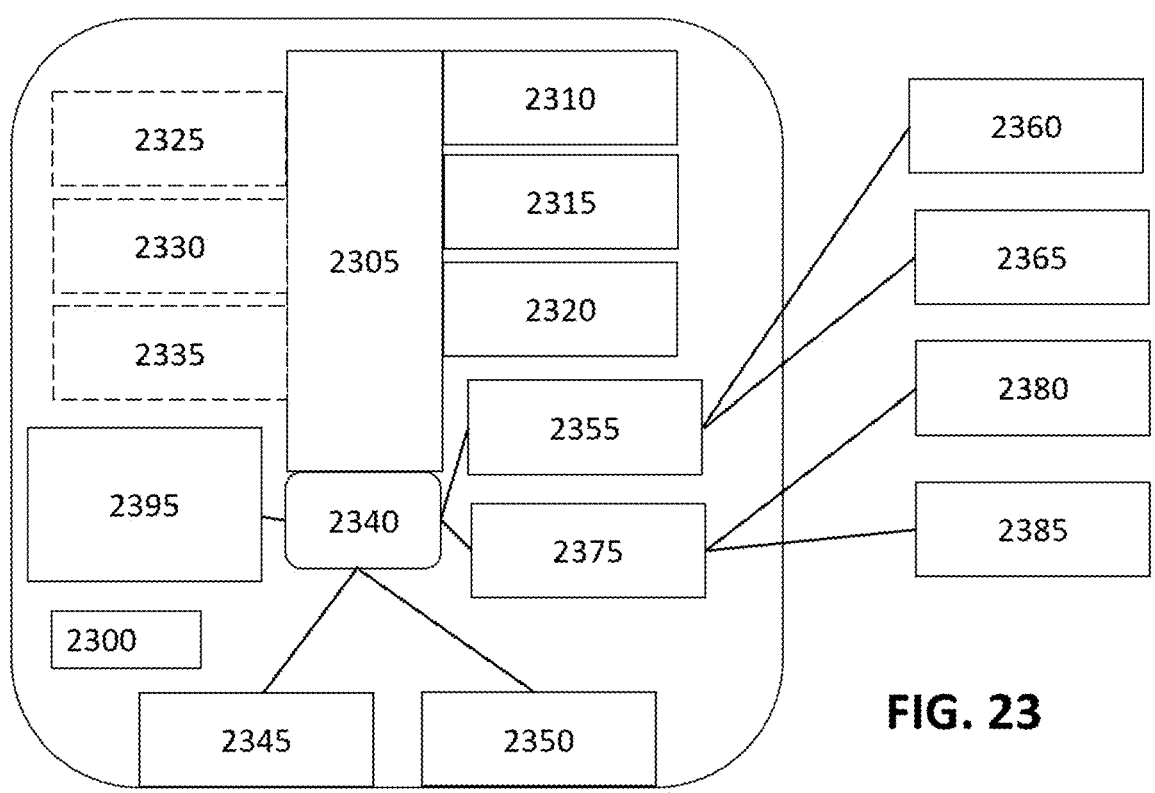
FIG. 23 is a system diagram of a neural-stimulation device for delivery of transcranial Electrical Stimulation and acquisition of EEG data.

Electrode arrays can be arranged around the patient's brain (either directly or indirectly through layers of dura, skull, or skin). Furthermore, the electrodes and pulse sequence described herein may be arranged on any given region of the body on a mammal to stimulate any biological tissue, including transcranial current stimulation in the brain. FIG. 23 is a system diagram of a neural-stimulation device that may be attached to a headset such as shown in FIGS. 19 and 20. The device has two purposes, delivering the transCranial Electrical Stimulation, and, optionally, to record the EEG and, in some cases, processing the EEG and using the result to optimize the stimulation waveform and voltage gradient geometry. In some embodiments, the device is assembled on board 2300 with high-speed communication mediated through Internal Communications Bus 2305 with major components CPU 2310, RAM Memory 2315, ROM Memory 2320 and, optionally, Al/Machine Learning Processor(s) 2325, an Encryption Processor 2330, and a Special-Purpose Processor 2335. Internal Communications Bus 2305 is connected to Power and Communications Interface 2340 that provides interfaces to Battery Supply 2395, the External Communications Interface 2345 that may be a wired and/or wireless and provide functions such as importing control instructions such as, but not limited to, which waveform(s) to deliver, updating software, and exporting information such as EEG data, the User Interface 2350 (mechanical switches and lights for example), Electrical Stimulation Output Controller 2355, and EEG Data Acquisition Module 2375. Electrical Stimulation Output Controller 2355 is interfaced to Electrode Arrays 2360 and 2365. The stimulation output is distributed to the cathode and anode electrode arrays in a manner to produce the applicable scalar curvatures of the voltage gradient geometry. EEG Data Acquisition Module 2375 receives input from EEG Electrode Sets 2380 and 2385.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention.

The invention claimed is:

1. A device comprising:
   a plurality of stimulating and EEG sensing electrode-contacts configured to be placed around a region of interest of biological tissue, the stimulating electrode contacts selected from the group consisting of non-invasive, minimally invasive, and invasive and configured such that each electrode-contact generates a plurality of voltage-gradient geometries through the region of interest including a neural tract to at least a subset of other electrode-contacts;
   a voltage-gradient geometry is selected from the group consisting of disparate, and local; and
   where a voltage-gradient curvature is selected from the group consisting of positive, zero, negative, and hybrid; and
   the plurality of stimulating and EEG sensing electrode-contacts are reconfigurable to measure electrical and magnetic potentials in biological tissue, the EEG sensing electrode-contacts selected from the group consisting of non-invasive, minimally invasive, or invasive; and
   a controller configured to selectively modulate a voltage-gradient waveform signal between sets of electrode-contacts through the region of interest to generate different orientations and shapes of voltage-gradient geometries between the electrode-contacts by
   modulating an analog or digital waveform signal using modulation selected from the group consisting of pulse-amplitude, pulse-width, pulse-frequency, and pulse-position based on;
   regression models analyzing one or more dependent variables and one or more independent variables to optimize the voltage-gradient geometry on which models are selected from the group consisting of linear regression, multiple regression, multiple target regression, empirically driven Bayesian optimization, theoretically driven Bayesian optimization, and hybrid driven Bayesian optimization;
   the dependent variables are selected from the group consisting of the independent dimensions of the cathode and anode electrode-contacts that are activated, the location on the plurality of electrode-contacts placed around a region of interest, the number of terminal points the voltage gradient has, the volume of the voltage gradient, the curvature of the voltage gradient, the unit charge per area of individual segments of the voltage gradient, the total charge of the total voltage gradient, the arc-length of the gradient, and the arc-path of the voltage gradient;
   the independent variables are generated from the group consisting of sensor devices, biomarkers, physiologic processes, healthcare workers, clinical instruments, and clinical outcomes;
   wherein the modulation of the voltage-gradient waveform signal is purposed to induce a specific physiological response in biological tissue;
   where each stimulating electrode-contact has sub-electrode-contacts and each sub-electrode-contact operate in a sub-electrode-contact group;

where each sub-electrode-contacts group operates with another sub-electrode-contact group in a sub-electrode-contact super-group (SESG);

where a SESG contains 1 to (n−1) sub-electrode-contact groups where n=# of sub-electrode-contact groups where each SESG can be combined in a sub-electrode-contact super-group network (SESGN) and the algorithm to determine the number of different SESG combinations of size n is: $a(n) = 3^{\wedge}(n-1) - 2 * 2^{\wedge}(n-1)$;

wherein electrode-contacts and sub-electrode-contacts are made from flexible circuits and conductive materials selected from, but not limited to, the group consisting of silver chloride, silver, gold, and stainless steel to account for different head topologies.

2. The device of claim 1, wherein the controller is further configured to repeatedly provide voltage-gradient waveform signals of pulses selected from the group consisting of electrical and magnetic at a rate between 0 Hz to 100 kHz a based on the group consisting of regression models, machine learning, independent user, and group of users.

3. The device of claim 1, wherein the controller is further configured to vary in time the firing of the subsets of sub-electrode-contacts at rates of 0 Hz to 100 kHz selected during a predetermined time as based on the group consisting of regression models, machine learning, independent user, and group of users.

4. The device of claim 1, wherein the controller is further configured to modulate the delivered voltage-gradient waveform signal parameters to optimize one or a plurality of characteristics of dependent variables selected from the group consisting of shape, orientation, and position relative to a neural tract being stimulated of the voltage-gradient geometry based on information gathered from the EEG sensing electrode contacts.

5. The device of claim 1, wherein the controller is further configured to selectively operate subsets of sub-electrode-contacts within arrays to form the sets of a sub-electrode-contact super-group network (SESGN) to modulate one or a plurality of characteristics selected from the group consisting of shape, orientation, and position relative to a neural tract being stimulated to generate the voltage-gradient geometries being delivered to a sub-electrode-contact super-group network (SESGN) at specific periods.

6. The device of claim 1 where the independent variables are generated by a closed-loop EEG and stimulating device.

* * * * *